US012187777B2

(12) United States Patent
Yang et al.

(10) Patent No.: US 12,187,777 B2
(45) Date of Patent: *Jan. 7, 2025

(54) ENGINEERED INVARIANT NATURAL KILLER T (iNKT) CELLS AND METHODS OF MAKING AND USING THEREOF

(71) Applicant: The Regents of the University of California, Oakland, CA (US)

(72) Inventors: Lili Yang, Los Angeles, CA (US); Drake J. Smith, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 640 days.

This patent is subject to a terminal disclaimer.

(21) Appl. No.: 17/172,925

(22) Filed: Feb. 10, 2021

(65) Prior Publication Data

US 2022/0372102 A1 Nov. 24, 2022

Related U.S. Application Data

(63) Continuation of application No. 15/320,037, filed as application No. PCT/US2015/039465 on Jul. 8, 2015, now Pat. No. 10,927,160.

(60) Provisional application No. 62/099,711, filed on Jan. 5, 2015, provisional application No. 62/022,301, filed on Jul. 9, 2014.

(51) Int. Cl.
*C12N 5/0783* (2010.01)
*A61K 48/00* (2006.01)
*C07K 14/705* (2006.01)
*C07K 14/725* (2006.01)
*A61K 39/00* (2006.01)

(52) U.S. Cl.
CPC .......... *C07K 14/7051* (2013.01); *A61K 48/00* (2013.01); *C07K 14/70503* (2013.01); *C12N 5/0646* (2013.01); *A61K 2039/5154* (2013.01); *C12N 2506/11* (2013.01); *C12N 2510/00* (2013.01); *C12N 2740/13043* (2013.01); *C12N 2830/48* (2013.01)

(58) Field of Classification Search
None
See application file for complete search history.

(56) References Cited

U.S. PATENT DOCUMENTS

| 10,927,160 | B2* | 2/2021 | Yang | A61K 39/4611 |
| 11,154,573 | B2* | 10/2021 | Crooks | A61K 39/4644 |
| 2005/0238626 | A1 | 10/2005 | Yang et al. | |
| 2013/0295142 | A1* | 11/2013 | Taniguchi | A61P 37/08 506/14 |
| 2013/0344095 | A1 | 12/2013 | Wang et al. | |
| 2015/0353889 | A1* | 12/2015 | Wakao | C07K 14/7051 435/325 |

FOREIGN PATENT DOCUMENTS

| EP | 2336303 | 6/2011 |
| WO | 2009009063 | 1/2009 |
| WO | 2012074116 | 6/2012 |

OTHER PUBLICATIONS

Watarai et al. (Blood. 2010;115:230-237). (Year: 2010).*
Office Action Issued in Corresponding European Patent Application No. EP 15819070.2, dated Nov. 11, 2019.
Vatakis, et al., "Antitumor Activity From Antigen-Specific CD8 T Cells Generated In Vivo From Genetically Engineered Human Hematopoietic Stem Cells," PNAS, 108(51): e1408-e1416, 2011.
Extended European Search Report received in EP15819070 mailed Dec. 12, 2017.
Bendelac, et al., "Increased Interleukin 4 and Immunoglobulin E Production in Transgenic Mice Overexpressing NK1 T cells", Oct. 1, 1996, pp. 1285-1293, vol. 184, Publisher: J_ Exp. Med.
Bilic, et al., "Concise Review: Induced Pluripotent Stem Cells Versus Embryonic Stem Cells: Close Enough or Yet Too Far Apart?", Dec. 23, 2011, p. 3341, vol. 30, Publisher: Stem Cells.
Medvedev, et al., "Induced Pluripotent Stem Cells: Problems and Advantages when Applying them in Regenerative Medicine", Oct. 4, 2010, vol. 2, No. 2(5), Publisher: Acta Naturae.
Panopoulos, et al., "Induced pluripotenl stem cells in clinical hematology: potentials, progress, and remaining Obslacles", pp. 1-5, vol. 19, No. 00, Publisher: Curr Opin Hemalol.
Ren, et al., "Generation of induced pluripotent stem cell-derived mice by reprogramming of a mature NKT cell", May 22, 2014, p. 551561, vol. 26, No. 10, Publisher: International Immunology.
Sun, et al., "Invariant natural killer T cells generated from human adult hematopoietic stem-progenitor cells are poly-functional", Jan. 5, 2015, pp. 48-57, vol. 72, Publisher: Cytokine.
Taniguchi, et al., "Essential requirement of an invariant V{alpha}14 T cell antigen receptor expression in the : developmenl of natural killer T cells", Oct. 1, 1996, pp. 11025-11028, vol. 93, Publisher: Proc. Nall. Acad. Sci. USA.
Vivier, et al., "Targeting natural killer cells and natural killer T cells in cancer", Apr. 1, 2012, pp. 239-252, vol. 12, Publisher: Nature Reviews Immunology.
Brennan, et al., "Invariant natural killer T cells: an innate activation scheme linked to diverse effector functions", Jan. 21, 2013, pp. 101-117, vol. 13, No. 2, Publisher: Nat. Rev. Immunol.
MGT_DQ341448, "*Homo sapiens* clone J3N.5 T cell receptor alpha chain mRNA, complete cds, Accession No. DQ34144, Version 10", May 22, 2013.
International Search Report received in PCT/US2015/039465, Dec. 14, 2015.
Matulis, et al., "Innate-Like Control of Human iNKT Cell Autoreactivity via the Hypervariable CDR3b Loop", Jun. 22, 2010, p. e100040, vol. 8, No. 6, Publisher: PLoS Biol.

(Continued)

*Primary Examiner* — Zachary S Skelding
(74) *Attorney, Agent, or Firm* — GATES & COOPER LLP

(57) ABSTRACT

Disclosed herein are invariant natural killer T (iNKT) cells engineered using hematopoietic stem and progenitor cells (HSPCs) and methods of making and using thereof.

13 Claims, 13 Drawing Sheets

Specification includes a Sequence Listing.

(56) References Cited

OTHER PUBLICATIONS

Written Opinion received in PCT/US2015/039465, Dec. 14, 2015.
Lantz, et al., "An invariant T cell receptor alpha chain is used by a unique subset of major histocompatibility complex class I-specific CD4+ and CD4-8-T cells in mice and humans", Sep. 1, 1994, pp. 1097-1106, vol. 180, No. 3, Publisher. J. Exp. Med.
Pilones, K.A., et al., "Invariant NKT cells as novel targets for immunotherapy in solid tumors", Sep. 2, 2012, pp. 1-11, vol. 2012, No. 720803, Publisher: Clin. Dev. Immunol.
Shissier et al. (Mol Immunol. Jan. 2019; 105: 116-130. doi:10.1016/j.mollimn.2018.09.023) (Year: 2019).
Van Kaer et al. (Immunotherapy. Published online Dec. 21, 2010; 3(1): 59-75) (Year: 2010).
Xu et al. (Nature Communications. (2018) 9:3875, p. 1-15) (Year: 2018).
Gilmore et al. (Experimental Hematology 28 (2000) 1297-1305). (Year: 2000).
Thedrez et al. (Blood. 2007; 110:251-258). (Year: 2007).
Sun et al. (Journal of Interferon & Cytokine Research. 2012; 32(11): 505-516). (Year: 2012).
Inoue et al. (Current Biology, vol. 15, 1114-1118, Jun. 21, 2005) (Year: 2005).

\* cited by examiner

ENGINEERED INVARIANT NATURAL KILLER T (iNKT) CELLS AND METHODS OF MAKING AND USING THEREOF

CROSS-REFERENCE TO RELATED APPLICATIONS

This application is a continuation application that claims the benefit under 35 U.S.C. § 121 of U.S. patent application Ser. No. 15/320,037, filed Dec. 19, 2016, which claims the benefit of U.S. Application No. 62/022,301, filed Jul. 9, 2014, and U.S. Application No. 62/099,711, filed Jan. 5, 2015, both of which are herein incorporated by reference in their entirety.

ACKNOWLEDGEMENT OF GOVERNMENT SUPPORT

This invention was made with Government support under DP2 CA196335 and P50 CA092131, awarded by the National Institutes of Health. The Government has certain rights in the invention.

REFERENCE TO A SEQUENCE LISTING SUBMITTED VIA EFS-WEB

The content of the ASCII text file of the sequence listing named "20150708_034044_149WO1_ST25" which is 21 kb in size was created on Jun. 30, 2015 and electronically submitted via EFS-Web herewith the application is incorporated herein by reference in its entirety.

BACKGROUND OF THE INVENTION

1. Field of the Invention

The present invention relates to invariant natural killer T (iNKT) cells engineered from hematopoietic stem and progenitor cells (HSPCs) and methods of making and using thereof.

2. Description of the Related Art

Invariant natural killer T (iNKT) cells are a small population of αβ T lymphocytes highly conserved from mice to humans. iNKT cells have been suggested to play important roles in regulating many diseases, including cancer, infections, allergies, and autoimmunity. When stimulated, iNKT cells rapidly release a large amount of effector cytokines like IFN-γ and IL-4, both as a cell population and at the single-cell level. These cytokines then activate various immune effector cells, such as natural killer (NK) cells and dendritic cells (DCs) of the innate immune system, as well as CD4 helper and CD8 cytotoxic conventional αβ T cells of the adaptive immune system via activated DCs. Because of their unique activation mechanism, iNKT cells can attack multiple diseases independent of antigen- and MHC-restrictions, making them attractive universal therapeutic agents. Notably, because of the capacity of effector NK cells and conventional αβ T cells to specifically recognize diseased tissue cells, iNKT cell-induced immune reactions result in limited off-target side effects.

In the past 2 decades, a series of iNKT cell-based clinical trials have been conducted, mainly targeting cancer. A recent trial reported encouraging antitumor immunity in patients with head and neck squamous cell carcinoma, attesting to the potential of iNKT cell-based immunotherapies. However, most clinical trials to date have yielded unsatisfactory results since they are based on the direct stimulation or ex vivo expansion of endogenous iNKT cells, thereby yielding only short-term, limited clinical benefits to a small number of patients. The low frequency and high variability of iNKT cells in humans (about 0.01-1% in blood), as well as the rapid depletion of these cells post-stimulation, are considered to be the major stumbling blocks limiting the success of these trials.

iNKT cells have been engineered from induced pluripotent stem (iPS) cells. See U.S. Pat. No. 8,945,922. iPS cells are produced by transducing a somatic cell with exogenous nuclear reprogramming factors, Oct4, Sox2, Klf4, and c-Myc, or the like. Unfortunately, since the transcription level of the exogenous nuclear reprogramming factors decreases with cell transition into the pluripotent state, the efficiency of stable iPS cell line production can decrease. Additionally, transcription of the exogenous nuclear reprogramming factors can resume in iPS cells and cause neoplastic development from cells derived from iPS cells since Oct4, Sox2, Klf4, and c-Myc are oncogenes that lead to oncogenesis. See Medvedev, et al. (2010) Acta Naturae 2(5):18-27.

Thus, a need exists for engineered iNKT cells that are not derived from iPS cells.

SUMMARY OF THE INVENTION

In some embodiments, the present invention provides an engineered cell which is a cell genetically modified to contain at least one exogenous invariant natural killer T cell receptor (iNKT TCR) nucleic acid molecule. In some embodiments, the cell is a hematopoietic stem cell. In some embodiments, the cell is a hematopoietic progenitor cell. In some embodiments, the cell is a human cell. In some embodiments, the cell is a $CD34^+$ cell. In some embodiments, the cell is a human $CD34^+$ cell. In some embodiments, the cell is a recombinant cell. In some embodiments, the cell is of a cultured strain. In some embodiments, the iNKT TCR nucleic acid molecule is from a human invariant natural killer T cell. In some embodiments, the iNKT TCR nucleic acid molecule comprises one or more nucleic acid sequences obtained from a human iNKT TCR. In some embodiments, the iNKT TCR nucleic acid sequence can be obtained from any subset of iNKT cells, such as the CD4/DN/CD8 subsets or the subsets that produce Th1, Th2, or Th17 cytokines, and includes double negative iNKT cells. In some embodiments, the iNKT TCR nucleic acid sequence is obtained from an iNKT cell from a donor who had or has a cancer such as melanoma, kidney cancer, lung cancer, prostate cancer, breast cancer, lymphoma, leukemia, a hematological malignancy, and the like. In some embodiments, the iNKT TCR nucleic acid molecule has a TCRα sequence from one iNKT cell and a TCRβ sequence from a different iNKT cell. In some embodiments, the iNKT cell from which the TCRα sequence is obtained and the iNKT cell from which the TCRβ sequence is obtained are from the same donor. In some embodiments, the donor of the iNKT cell from which the TCRα sequence is obtained is different from the donor of the iNKT cell from which the TCRβ sequence is obtained. In some embodiments, the TCRα sequence and/or the TCRβ sequence are codon optimized for expression. In some embodiments, the TCRα sequence and/or the TCRβ sequence are modified to encode a polypeptide having one or more amino acid substitutions, deletions, and/or truncations compared to the polypeptide encoded by the unmodified sequence. In some embodiments, the iNKT TCR nucleic acid molecule encodes a T cell receptor that recognizes α-galactosylceramide (α-GalCer) presented on CD1d. In some embodiments, the iNKT TCR nucleic acid molecule comprises one or more sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 18, SEQ ID NO: 19, SEQ ID NO: 21, SEQ ID NO: 22, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, SEQ ID NO: 52, SEQ ID NO: 54, SEQ ID NO: 55, SEQ ID NO: 57, SEQ ID NO: 58, SEQ ID NO: 60, and SEQ ID NO: 61. In some embodiments, the iNKT TCR nucleic acid molecule encodes a polypeptide comprising an amino acid sequence selected from the group consisting of: SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, SEQ ID NO: 56, SEQ ID NO: 59, and SEQ ID NO: 62. In some embodiments, the engineered cell lacks exogenous oncogenes, such as Oct4, Sox2, Klf4, c-Myc, and the like. In some embodiments, the engineered cell is a functional iNKT cell. In some embodiments, the engineered cell is capable of producing one or more cytokines and/or chemokines such as IFNγ, TNFα, TGFβ, GM-CSF, IL-2, IL-4, IL-5, IL-6, IL-10, IL-13, IL-17, IL-21, RANTES, Eotaxin, MIP-1α, MIP-1β, and the like.

In some embodiments, the present invention provides a method obtaining an engineered cell of the present invention, which comprises transducing the cell with at least one exogenous invariant natural killer T cell receptor (iNKT TCR) nucleic acid molecule. In some embodiments, the cell is a hematopoietic stem cell. In some embodiments, the cell is a hematopoietic progenitor cell. In some embodiments, the cell is a human cell. In some embodiments, the cell is a CD34⁺ cell. In some embodiments, the cell is a human CD34⁺ cell. In some embodiments, the cell is a recombinant cell. In some embodiments, the cell is of a cultured strain. In some embodiments, the iNKT TCR nucleic acid molecule is from a human invariant natural killer T cell. In some embodiments, the iNKT TCR nucleic acid molecule comprises one or more nucleic acid sequences obtained from a human iNKT TCR. In some embodiments, the iNKT TCR nucleic acid sequence can be obtained from any subset of iNKT cells, such as the CD4/DN/CD8 subsets or the subsets that produce Th1, Th2, or Th17 cytokines, and includes double negative iNKT cells. In some embodiments, the iNKT TCR nucleic acid sequence is obtained from an iNKT cell from a donor who had or has a cancer such as melanoma, kidney cancer, lung cancer, prostate cancer, breast cancer, lymphoma, leukemia, a hematological malignancy, and the like. In some embodiments, the iNKT TCR nucleic acid molecule has a TCRα sequence from one iNKT cell and a TCRβ sequence from a different iNKT cell. In some embodiments, the iNKT cell from which the TCRα sequence is obtained and the iNKT cell from which the TCRβ sequence is obtained are from the same donor. In some embodiments, the donor of the iNKT cell from which the TCRα sequence is obtained is different from the donor of the iNKT cell from which the TCRβ sequence is obtained. In some embodiments, the TCRα sequence and/or the TCRβ sequence are codon optimized for expression. In some embodiments, the TCRα sequence and/or the TCRβ sequence are modified to encode a polypeptide having one or more amino acid substitutions, deletions, and/or truncations compared to the polypeptide encoded by the unmodified sequence. In some embodiments, the iNKT TCR nucleic acid molecule encodes a T cell receptor that recognizes α-galactosylceramide (α-GalCer) presented on CD1d. In some embodiments, the iNKT TCR nucleic acid molecule comprises one or more sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 18, SEQ ID NO: 19, SEQ ID NO: 21, SEQ ID NO: 22, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, SEQ ID NO: 52, SEQ ID NO: 54, SEQ ID NO: 55, SEQ ID NO: 57, SEQ ID NO: 58, SEQ ID NO: 60, and SEQ ID NO: 61. In some embodiments, the iNKT TCR nucleic acid molecule encodes a polypeptide comprising an amino acid sequence selected from the group consisting of: SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, SEQ ID NO: 56, SEQ ID NO: 59, and SEQ ID NO: 62. In some embodiments, the engineered cell lacks exogenous oncogenes, such as Oct4, Sox2, Klf4, c-Myc, and the like. In some embodiments, the engineered cell is a functional iNKT cell. In some embodiments, the engineered cell is capable of producing one or more cytokines and/or chemokines such as IFNγ, TNFα, TGF1β, GM-CSF, IL-2, IL-4, IL-5, IL-6, IL-10, IL-13, IL-17, IL-21, RANTES, Eotaxin, MIP-1α, MIP-1β, and the like. In some embodiments, the method further comprises expanding the cell transduced with the iNKT TCR nucleic acid sequence in vitro. In some embodiments, the method further comprises engrafting the cell transduced with the iNKT TCR nucleic acid molecule in a subject to generate clonal populations of the engineered cell. In some embodiments, the subject contains human thymus tissue. In some embodiments, the subject is an animal such as a mouse. In some embodiments, the subject is human. In some embodiments, the method further comprises culturing the cell transduced with the iNKT TCR nucleic acid molecule with OP9-DL1 stromal cells and then culturing with CD1d-expressing artificial antigen-presenting cells. In some embodiments, the method further comprises culturing the cell transduced with the iNKT TCR nucleic acid molecule with MS5-DL4 stromal cells and then culturing with CD1d-expressing artificial antigen-presenting cells. In some embodiments, the method further comprises cloning the T cell receptor of an invariant natural killer T (iNKT) cell. In some embodiments, the iNKT cell is obtained from a donor. In some embodiments, the iNKT cell is obtained from a subject to be treated with the engineered cell. In some embodiments, the iNKT cell is obtained from an animal such as a mouse. In some embodiments, the iNKT cell is obtained from a human. In some embodiments, the iNKT TCR nucleic acid molecule is contained in an expression vector. In some embodiments, the expression vector is a lentiviral expression vector. In some embodiments, the expression vector is a MIG vector in which the iNKT TCR nucleic acid molecule replaces the IRES-EGFP segment of the MIG vector. In some embodiments, the expression vector is phiNKT-EGFP.

In some embodiments, the present invention provides a composition comprising one or more engineered cells of the present invention and/or one or more engineered cells made by a method according to the present invention. In some embodiments, the compositions comprise the one or more engineered cells at a concentration of about $1.0 \times 10^5$ to $1.0 \times 10^7$ cells/ml. In some embodiments, the composition further comprises a pharmaceutically acceptable carrier. In some embodiments, the composition further comprises a medium suitable for culturing the engineered cells. In some embodiments, the composition further comprises a cryopreservation medium. In some embodiments, the composition further comprises one or more agents that activate iNKT cells, e.g., α-GalCer or salts or esters thereof, α-GalCer-presenting dendritic cells, or artificial APCs.

In some embodiments, the present invention provides kits comprising one or more engineered cells or compositions according to the present invention packaged together with a drug delivery device, e.g., a syringe, for delivering the engineered cells or compositions to a subject. In some embodiments, the present invention provides kits comprising one or more engineered cells or compositions according to the present invention packaged together with one or more reagents for culturing and/or storing the engineered cells. In some embodiments, the present invention provides kits comprising one or more engineered cells or compositions according to the present invention packaged together with one or more agents that activate iNKT cells. In some embodiments, the present invention provides kits comprising one or more engineered cells or compositions according to the present invention packaged together with OP9-DL1 stromal cells and/or MS5-DL4 stromal cells. In some embodiments, the present invention provides kits comprising one or more engineered cells or compositions according to the present invention packaged together with antigen-presenting cells or CD1d-expressing artificial antigen-presenting cells.

In some embodiments, the present invention provides a method of treating a subject, which comprises administering to the subject one or more engineered cells according to the present invention, one or more engineered cells made according to a method of the present invention, or one or more compositions according to the present invention. In some embodiments, the subject is an animal such as a mouse or a test animal. In some embodiments, the subject is a human. In some embodiments, the subject is in need of treatment with iNKT cells. In some embodiments, the subject has a cancer, a bacterial infection, a viral infection, an allergy, or an autoimmune disease. In some embodiments, the cancer is melanoma, kidney cancer, lung cancer, prostate cancer, breast cancer, lymphoma, leukemia, or a hematological malignancy. In some embodiments, the subject has tuberculosis, HIV, or hepatitis. In some embodiments, the subject has asthma or eczema. In some embodiments, the subject has Type I diabetes, multiple sclerosis, or arthritis. In some embodiments, the subject is administered a therapeutically effective amount of the one or more engineered cells. In some embodiments, the therapeutically effective amount of the one or more engineered cells is about $10^7$ to about $10^9$ cells per kg body weight of the subject being treated. In some embodiments, the method further comprises administering an agent that activates iNKT cells, e.g., α-GalCer or salts or esters thereof, α-GalCer-presenting dendritic cells or artificial APCs, before, during, and/or after administration of the one or more engineered cells.

In some embodiments, the present invention provides medicaments and methods of making medicaments for treating subjects in need of treatment with iNKT cells, said medicaments comprise a therapeutically effective amount of one or more engineered cells according to the present invention. In some embodiments, the medicaments comprise a concentration of about $1.0 \times 10^5$ to about $1.0 \times 10^7$ cells/ml of a pharmaceutically acceptable carrier or diluent. In some embodiments, the medicaments comprise a concentration of about $1.0 \times 10^5$ to about $1.0 \times 10^6$ cells/ml of a pharmaceutically acceptable carrier or diluent. In some embodiments, the medicaments comprise a concentration of about $1.0 \times 10^6$ to about $1.0 \times 10^7$ cells/ml of a pharmaceutically acceptable carrier or diluent. In some embodiments, the medicaments can comprise a concentration that is higher than $1.0 \times 10^7$ cells/ml. In some embodiments, the medicaments comprise about $1 \times 10^7$ to about $1 \times 10^9$ of the one or more engineered cells. In some embodiments, the medicaments comprise about $1 \times 10^7$ to about $1 \times 10^8$ of the one or more engineered cells. In some embodiments, the medicaments comprise about $1 \times 10^8$ to about $1 \times 10^9$ of the one or more engineered cells.

In some embodiments, the present invention provides use of one or more engineered cells according to the present invention in the manufacture of a medicament for treating a subject in need of treatment with iNKT cells. In some embodiments, the medicaments comprise a therapeutically effective amount of the one or more engineered cells.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein (in the drawings, "HSC" refers to "HSPC"):

FIG. 1A shows a representative FACS plot. Single iNKT cells were sorted out from mouse spleen cells using flow cytometry based on a stringent collection of surface markers (gated as $CD3^{lo}mCD1d/PBS-57^+TCR\ V\beta8^+NK1.1^{hi}$). mCD1d/PBS-57 indicates the tetramer reagent that specifically stains mouse iNKT TCRs.

FIG. 1B shows a representative DNA gel showing the TCR α and β chain gene PCR products from five iNKT cells. Sorted single iNKT cells were subjected to TCR cloning using a single-cell RT-PCR approach.

FIG. 1C shows representative sequencing results confirming the cloned single-cell iNKT TCR α and β chain genes. The top 5 sequences for iNKT TCRα are SEQ ID NO: 1, and for the iNKT TCR β sequences (the bottom 5 sequences), from top to bottom, the SEQ ID NOs are: SEQ ID NO: 2, SEQ ID NO: 3, SEQ ID NO: 4, SEQ ID NO: 5, and SEQ ID NO: 6.

FIG. 1D is a schematic representation of the retroviral vectors encoding either a control EGFP reporter gene (denoted as the Mock vector), or a pair of iNKT TCR α and 13 chain genes (denoted as the miNKT vector). LTR indicates long-term repeats; IRES, internal ribosome entry sites;

EGFP, enhanced green fluorescence protein; F2A, foot-and-mouth disease virus 2A sequence; and WRE, woodchuck responsive element.

Figure 1A:
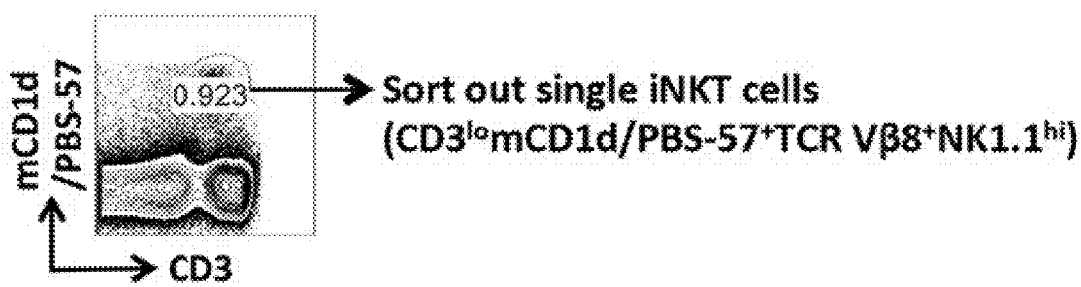
FIGS. 1A-1F schematically show the cloning of invariant natural killer T-cell receptor (iNKT TCR) genes, construction of retroviral delivery vectors, and expression of clonal iNKT TCRs.
Figure 1B:
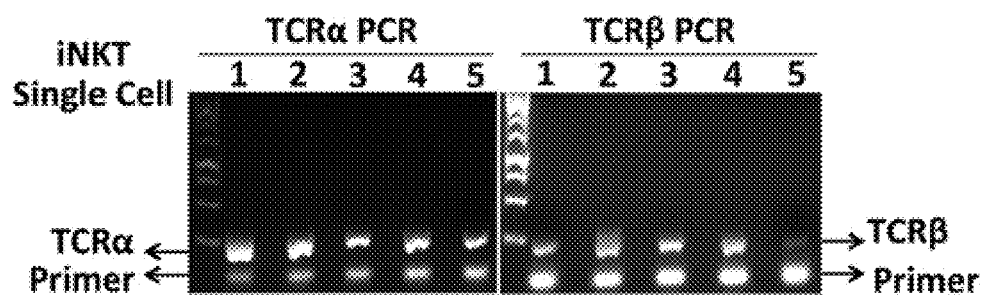
Figure 1C:
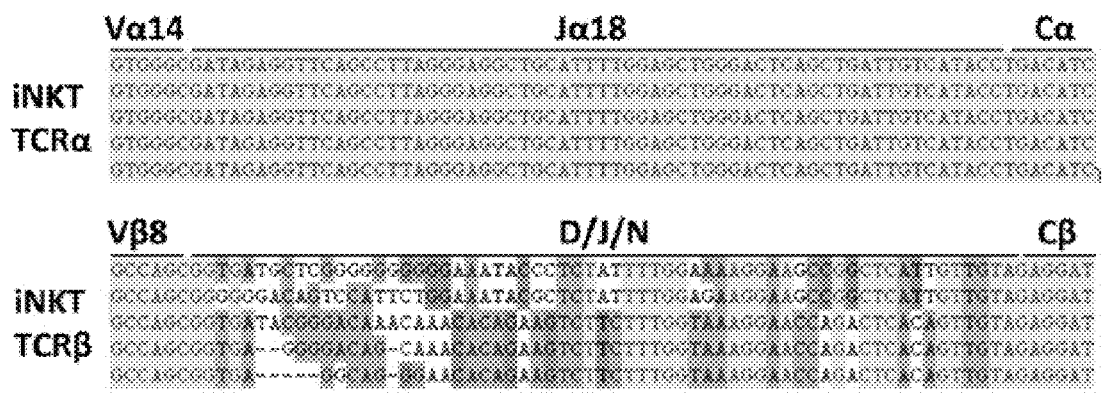
Figure 1D:
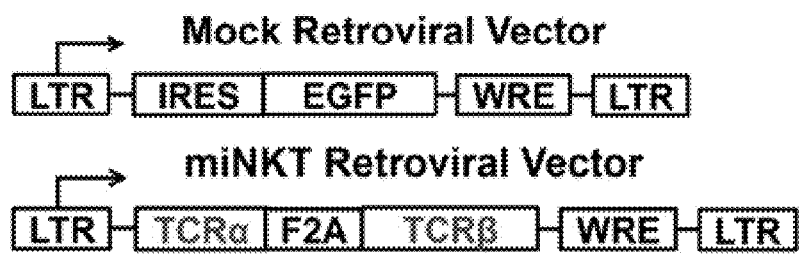
Figure 1E:
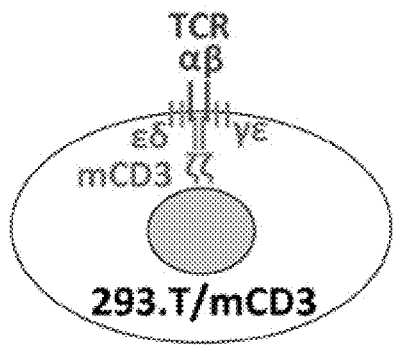

FIG. 1E is a schematic representation of the 293.T cell line that has been engineered to stably express mouse CD3 genes and so as to support the surface display of mouse TCRs (denoted as 293.T/mCD3).

Figure 1F:
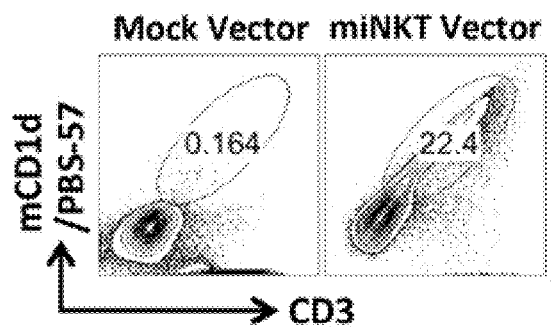

FIG. 1F are representative FACS plots showing the expression of clonal iNKT TCRs in 293.T/mCD3 cells transduced with the chosen miNKT vector.

FIGS. 2A-2K show the generation of functional iNKT cells through TCR gene engineering of hematopoietic stem cells (HSCs) and the characteristics of the HSPC-iNKT cells. B6 mice receiving adoptive transfer of HSCs transduced with either the Mock retroviral vector (denoted as B6-Mock mice) or miNKT retroviral vector (denoted as B6-miNKT mice) were allowed to reconstitute their immune system in a duration of 6-8 weeks, followed by analysis. The experiments were repeated at least three times, and representative results are presented. HSPC-iNKT cells were detected as TCR$\beta^{lo}$mCD1d/PBS-57$^+$ using flow cytometry.

Figure 2A:
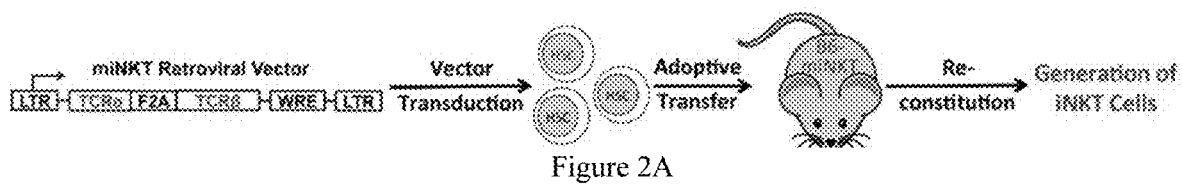

FIG. 2A is a schematic representation of the experimental design to generate HSPC-iNKT cells in mice.

Figure 2B:
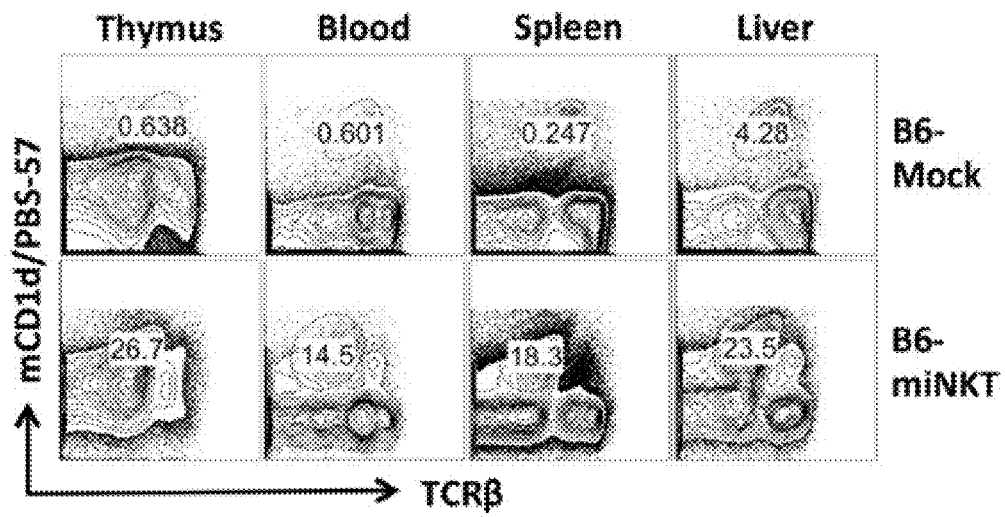
Figure 2C:
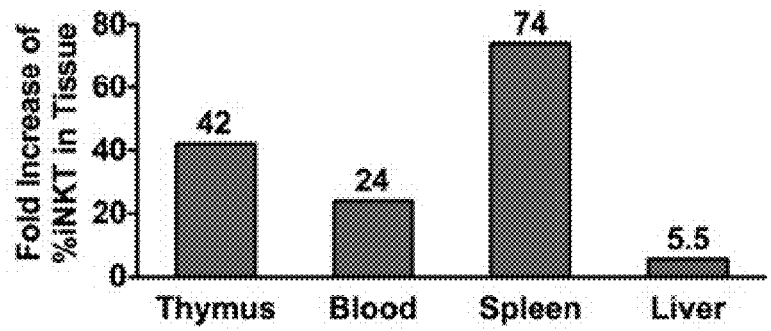

FIGS. 2B and 2C show an increase of iNKT cells in B6-miNKT mice compared with that in the control B6-Mock mice. FIG. 2B are FACS plots showing the detection of iNKT cells in various tissues. FIG. 2C are bar graphs showing the fold increase of percent iNKT cells in the indicated tissues.

Figure 2D:
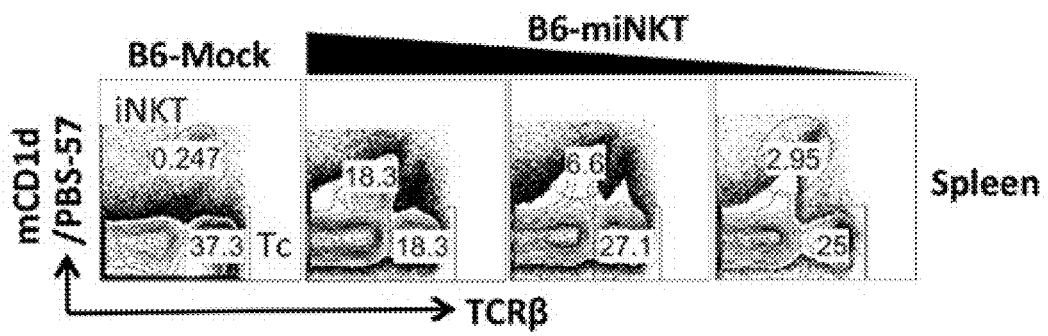
Figure 2E:
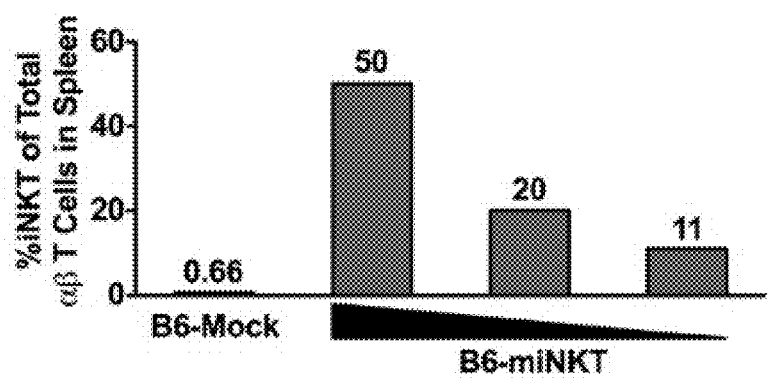

FIGS. 2D and 2E show control of iNKT cell numbers in B6-miNKT mice through titrating the miNKT vector-transduced HSPCs used for adoptive transfer. FIG. 2D are FACS plots showing the detection of iNKT cells in the spleens of various B6-miNKT recipient mice. Tc indicates the conventional αβ T cells (gated as TCRβ$^+$mCD1d/PBS-57$^-$). FIG. 2E are bar graphs showing the percent iNKT of total αβ T cells in spleen.

Figure 2F:
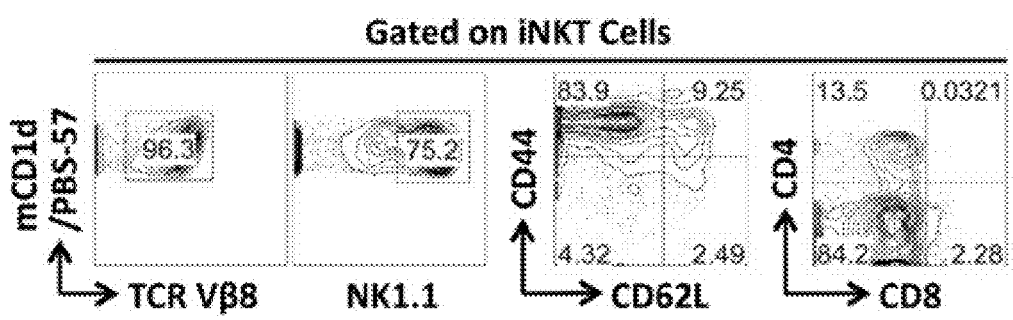

FIG. 2F are FACS plots showing the phenotype of the HSPC-iNKT cells. FACS plots are presented showing the surface markers of iNKT cells detected in the liver of B6-miNKT mice.

Figure 2G:
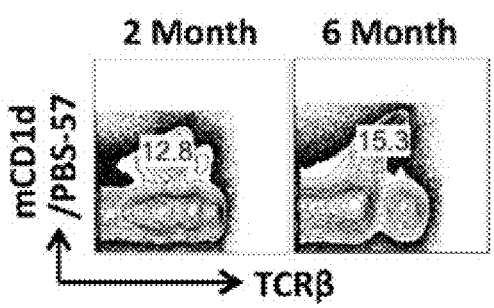
Figure 2H:
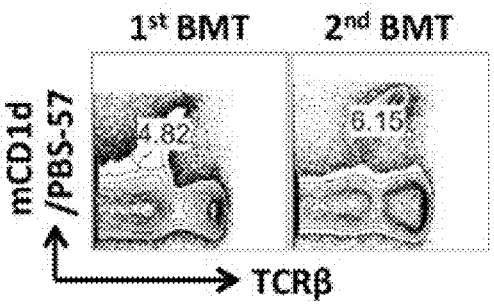

FIGS. 2G and 2H show long-term production of HSPC-iNKT cells. FACS plots are presented showing the detection of HSPC-iNKT cells in the spleen of B6-miNKT mice for up to 6 months after initial HSPC adoptive transfer (FIG. 2G) and at 2 months after secondary bone marrow transfer (BMT) (FIG. 2H).

Figure 2I:
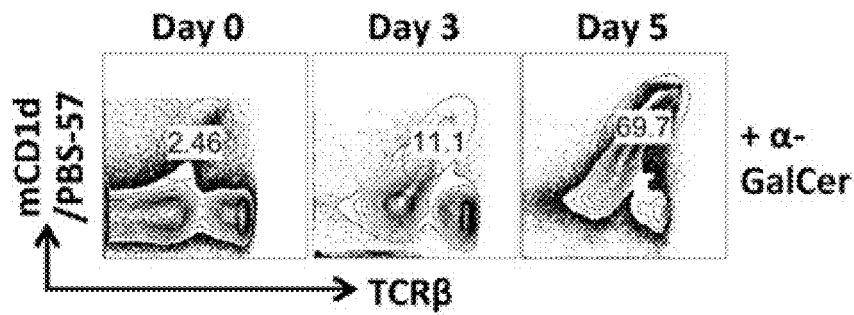
Figure 2J:
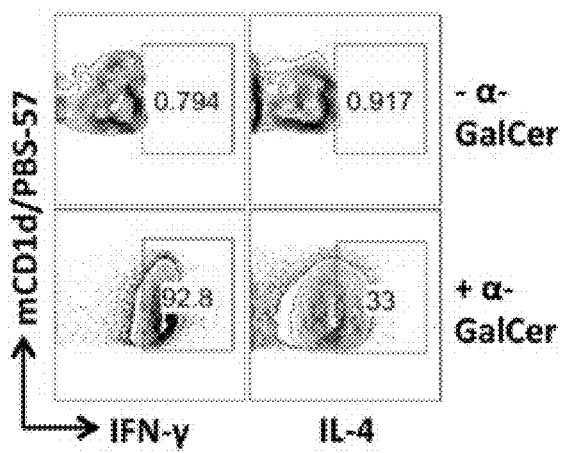
Figure 2K:
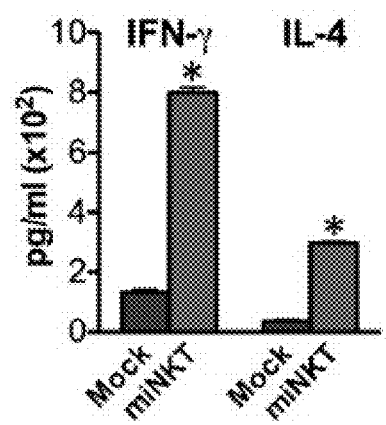

FIGS. 2I-2K show the functionality of the HSPC-iNKT cells tested in vitro. Spleen cells of B6-miNKT mice were cultured in vitro in the presence of α-GalCer (100 ng/mL). FIG. 2I are FACS plots showing the time-course proliferation of HSPC-iNKT cells. FIG. 2J are FACS plots showing the cytokine production in HSPC-iNKT cells on Day 3, as measured by intracellular cytokine staining. FIG. 2K are bar graphs of the ELISA analysis of cytokine production in the cell culture medium at Day 3. Data are presented as mean of duplicate cultures±SEM, *P<0.01 (B6-miNKT samples compared with the corresponding B6-Mock controls).

Figure 2L:
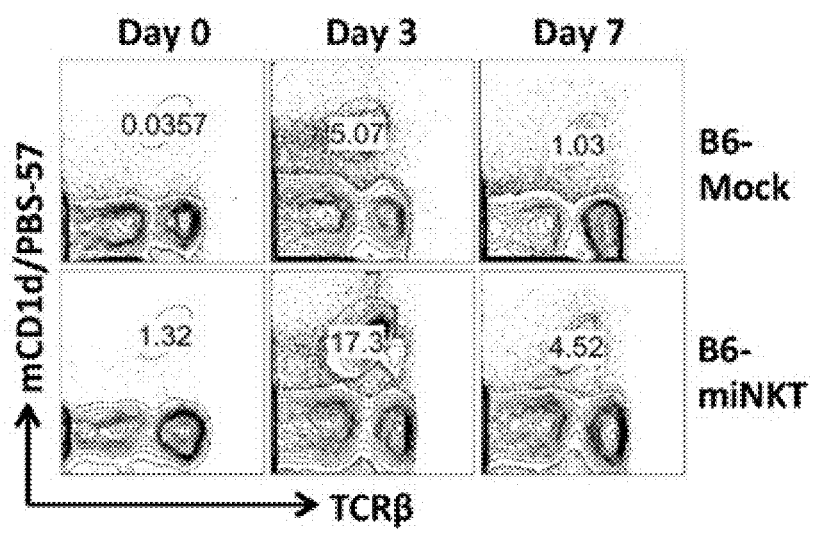

FIG. 2L are FACS plots showing the functionality of the HSPC-iNKT cells tested in vivo. B6-Mock or B6-miNKT mice were given i.v. injection of 1×10$^6$ bone marrow-derived dendritic cells (BMDCs) loaded with α-GalCer (denoted as BMDC/α-GalCer) and then periodically bled to monitor iNKT cell responses. FACS plots are presented showing the change of iNKT cell frequencies in blood.

FIGS. 3A-3E shows the development of the HSPC-iNKT cells. B6-miNKT and control B6-Mock mice were analyzed for iNKT cell development at 6-8 weeks post HSPC transfer. The experiments were repeated at least three times, and representative results are presented. HSPC-iNKT cells were detected as TCRβ$^{lo}$mCD1d/PBS-57$^+$ using flow cytometry.

Figure 3A:
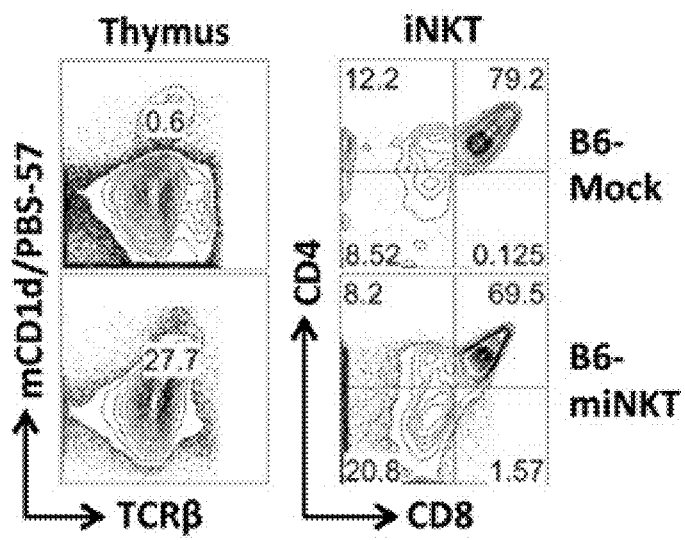
Figure 3B:
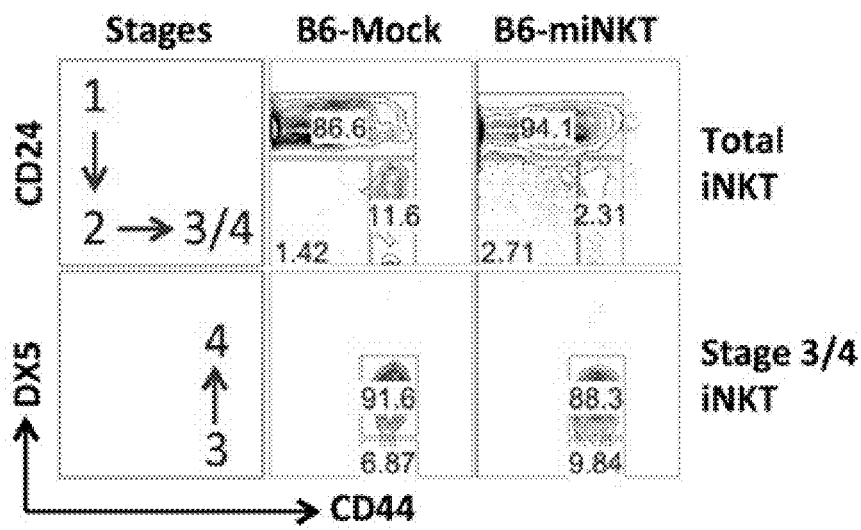

FIGS. 3A and 3B are FACS plots showing the characteristic development of HSPC-iNKT cells in thymus.

Figure 3C:
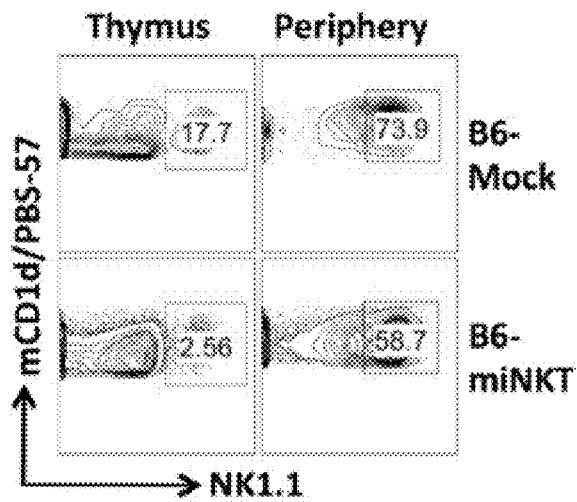

FIG. 3C are FACS plots showing the maturation of HSPC-iNKT cells in the periphery measured by the up-regulation of the NK1.1 marker. Comparisons of HSPC-iNKT cells from thymus and periphery (liver) are shown.

Figure 3D:
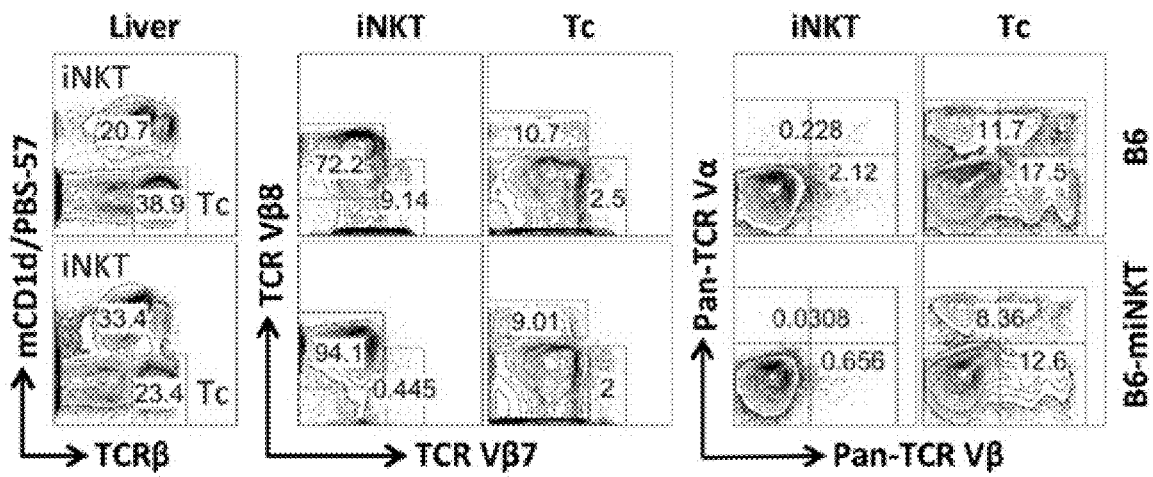
Figure 3E:
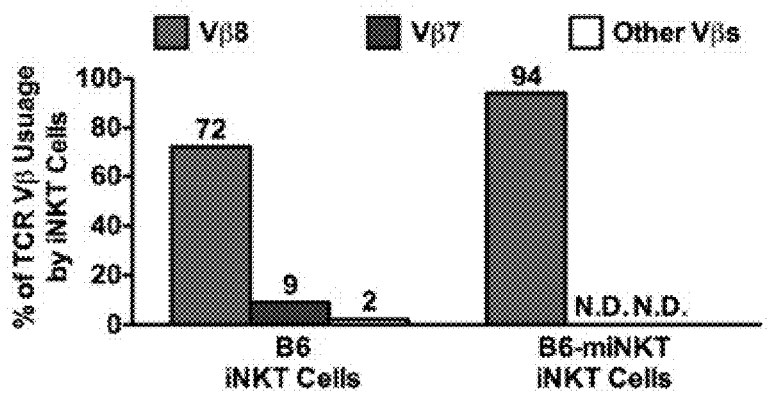

FIGS. 3D and 3E are FACS plots and bar graphs showing the exclusion of non-transgenic TCR expression on the HSPC-iNKT cells. Comparisons of iNKT and conventional αβ T (Tc) cells from the liver of B6-Mock or B6-miNKT mice are shown. Pan-TCR Vα panel includes Vα2, Vα3.2, and Vα8.3, whereas pan-TCR Vβ panel includes Vβ3, Vβ4, Vβ5, Vβ6, Vβ11, and Vβ13. N.D., not detected. As shown in FIG. 3E, the first bars of each set are Vβ8, the second bars of each set are Vβ7, and the third bars of each set are other Vβs.

FIGS. 4A-4F show protection from melanoma lung metastasis by the HSPC-iNKT cells. B6-miNKT and control B6-Mock mice were given i.v. injection of 0.5-1×10$^6$ B16.F10 melanoma cells on Day 0 and analyzed for melanoma lung metastasis on Day 14. On Day 3, experimental mice received i.v. injection of 1×10$^6$ BMDCs either unloaded or loaded with α-GalCer (denoted as BMDC/none or BMDC/α-GalCer, respectively) to mimic a therapeutic vaccine treatment. The experiments were repeated twice (5-7 mice per group), and representative results are presented.

Figure 4A:
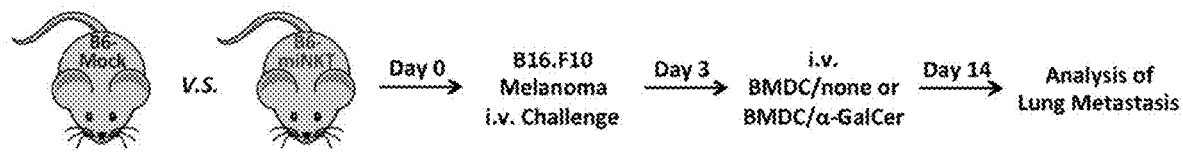

FIG. 4A is a schematic representation of the experimental design to study the cancer therapy potential of the HSPC-iNKT cells in the B16 melanoma lung metastasis mouse model.

Figure 4B:
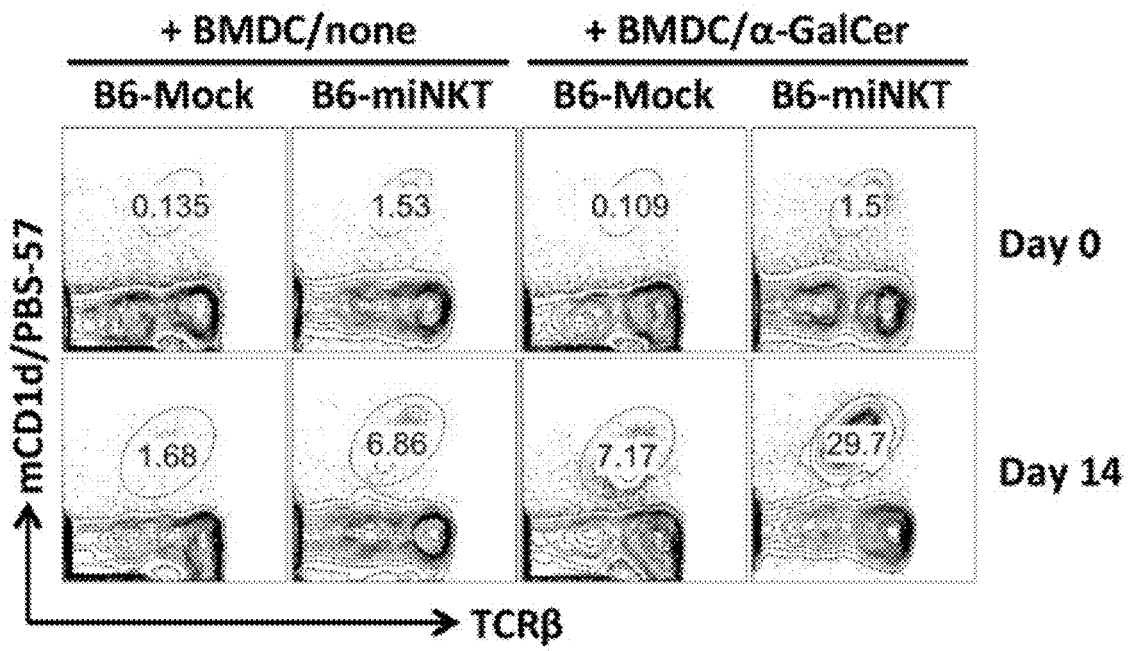

FIG. 4B are FACS plots showing the expansion of HSPC-iNKT cells in the blood of experimental mice in response to tumor challenge and BMDC/α-GalCer vaccination.

Figure 4C:
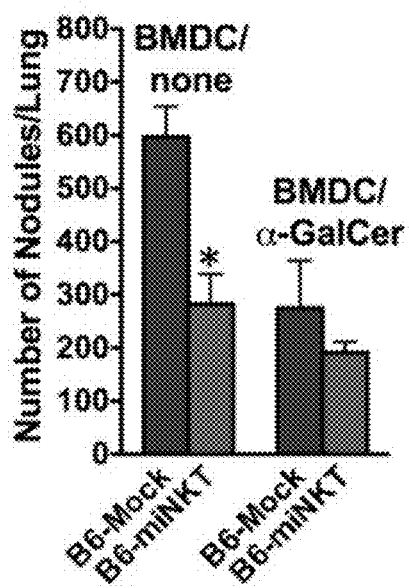
Figure 4D:
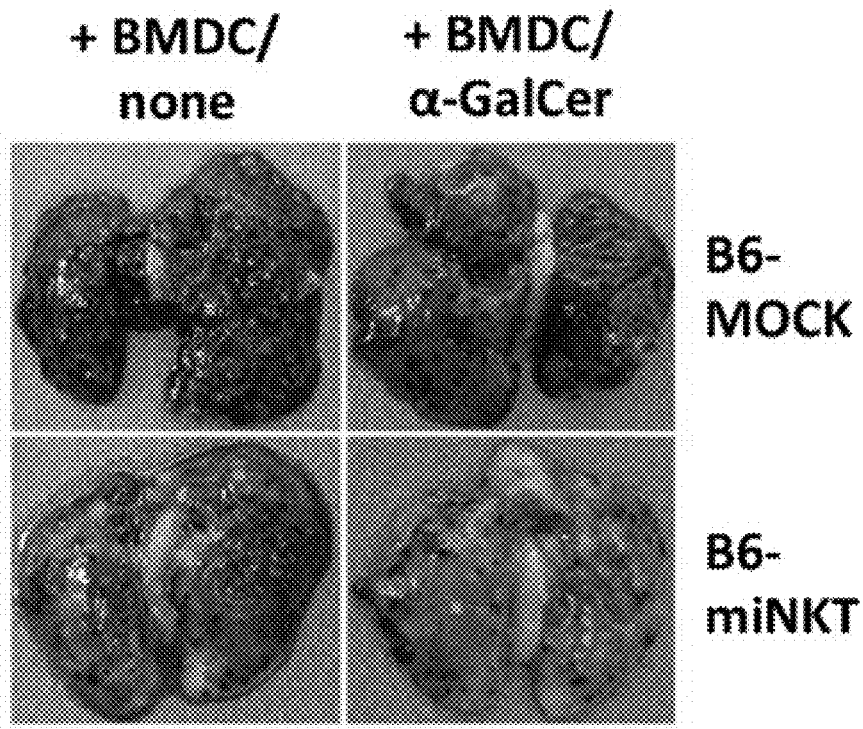
Figure 4E:
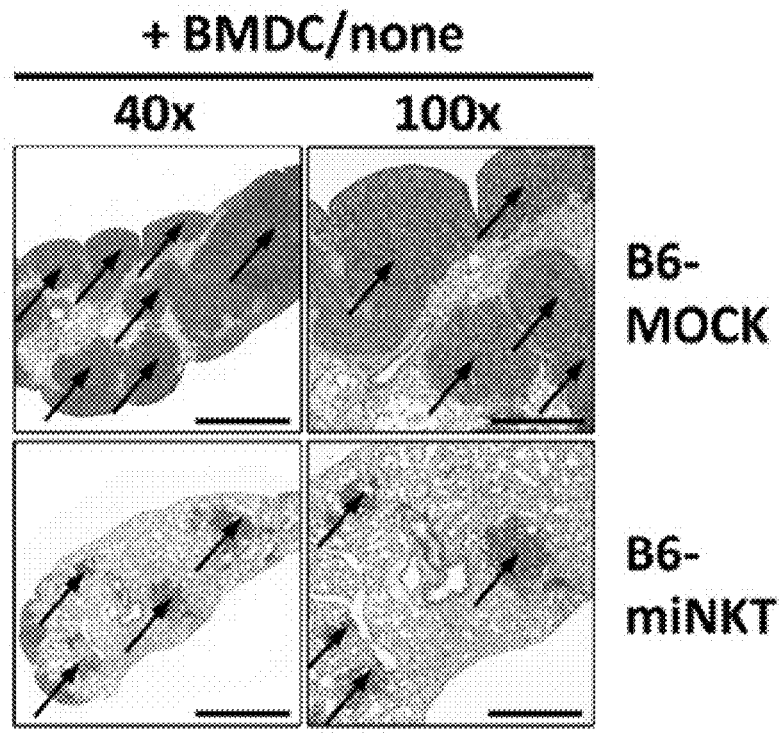
Figure 4F:
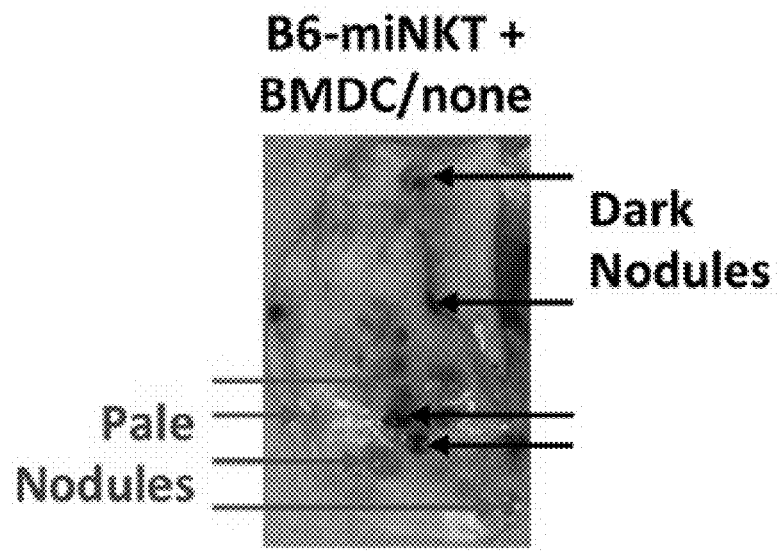

FIGS. 4C-4F show the analysis of melanoma lung metastasis in the experimental mice on Day 14. FIG. 4C is a bar graph showing the enumeration of lung tumor nodules. Data are presented as mean±SEM, *P<0.01 (B6-miNKT samples compared with corresponding B6-Mock controls). FIG. 4D are photos of lung showing melanoma metastasis. FIG. 4E are immunohistological lung sections with H-E staining. Metastatic tumor nodules are indicated by arrows. Bars: 1,000 μm (40× magnification); 500 μm (100× magnification). FIG. 4F is an image of a lung from a representative B6-miNKT mouse showing the detection of pale, depigmented tumor nodules.

Figure 5:
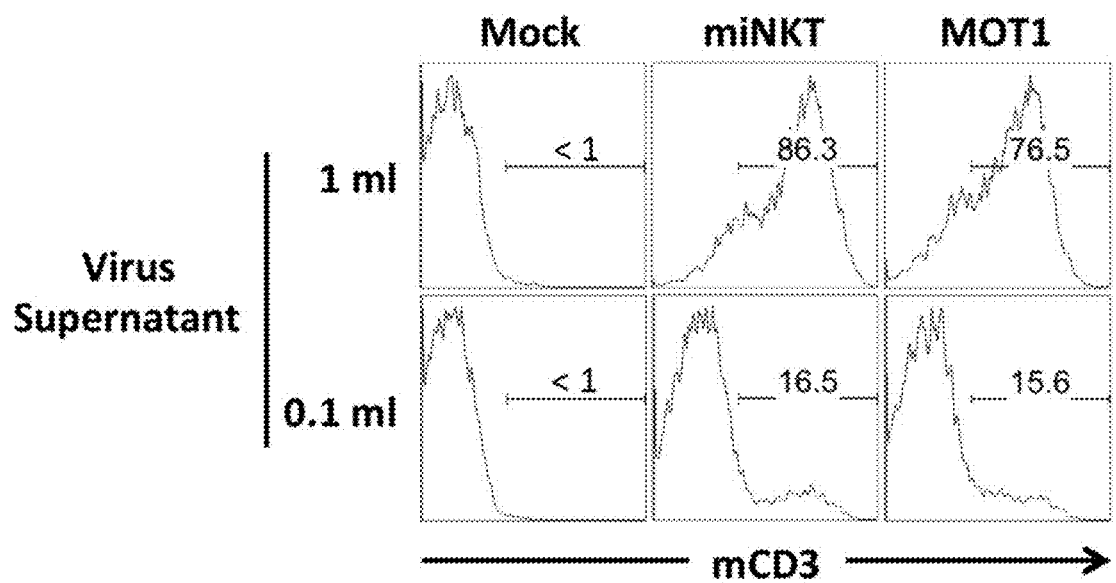

FIG. 5 are FACS plots showing the detection of mouse TCRs on cell surface. Titration of the miNKT retroviral vector. The 293.T/mCD3 cells were transduced with the titrated volume of indicated virus supernatants. Three days later, virus-mediated expression of mouse TCRs was measured using flow cytometry. Note mouse CD3 (mCD3) molecules only display on cell surface in complex with the transgenic mouse TCRs, therefore, they can be used as an indicator of transgenic TCR expression. The results show comparable titers of the miNKT and MOT1 retroviral vectors, estimated as about 0.5-1×10$^6$ IFU/mL (infectious units per milliliter). Mock, the control retroviral vector encoding an EGFP reporter gene; miNKT, the retroviral vector encoding a selected pair of mouse iNKT TCR α and β chain genes; MOT1, the retroviral vector encoding the α and β chain genes of OT1 TCR, a mouse conventional αβ TCR specific for chicken ovalbumin.

Figure 6A:
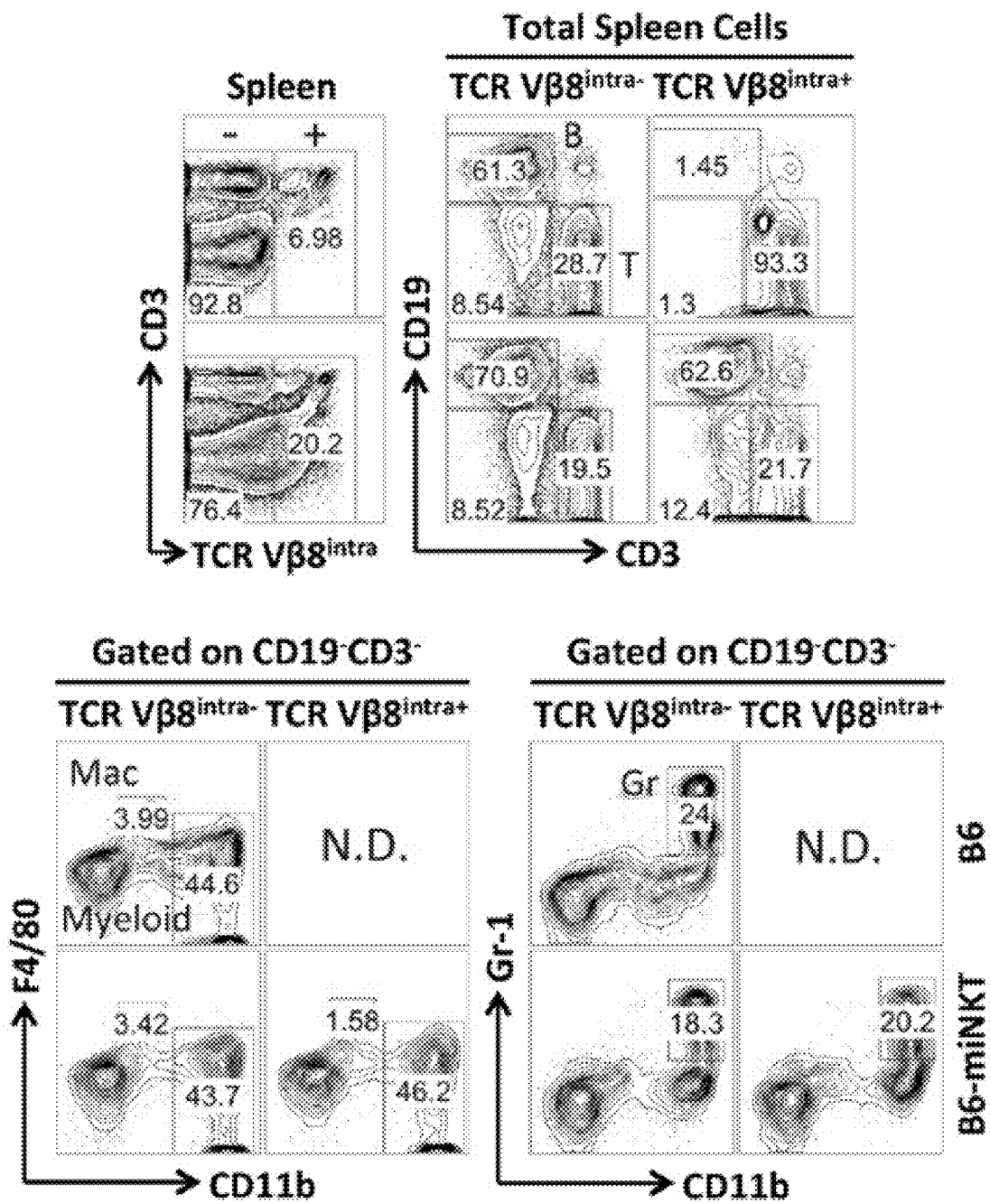
Figure 6B:
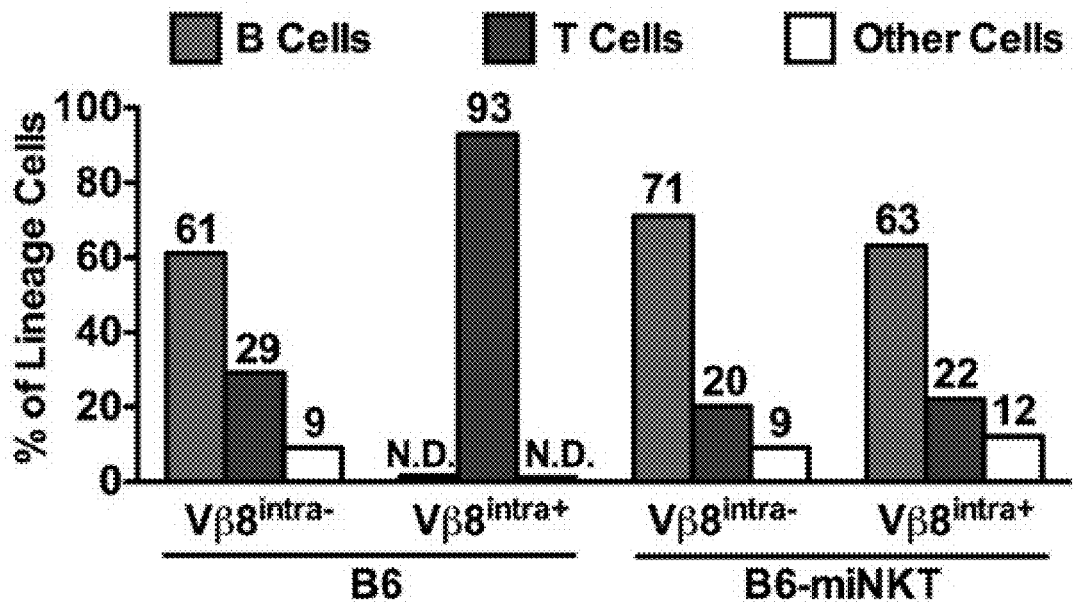

FIGS. 6A and 6B show lineage differentiation of TCR-transduced HSPCs. B6-miNKT and control B6-Mock mice were analyzed for the presence of HSPC-iNKT cells at 6-8 weeks post HSPC transfer. The experiments were repeated at least three times, and representative FACS plots (FIG. 6A) and bar graphs (FIG. 6B) are shown. Engineered cells were detected by intracellular staining of the transgenic TCRβ chain (gated as TCR Vβ8$^{intra+}$). Comparison analysis of the spleen cells of B6-miNKT and B6 control mice is presented. N.D., not detected. In the bar graphs, the first bars in each set are B cells, the second bars in each set are T cells, and the third bars in each set are other cells.

Figure 7A:
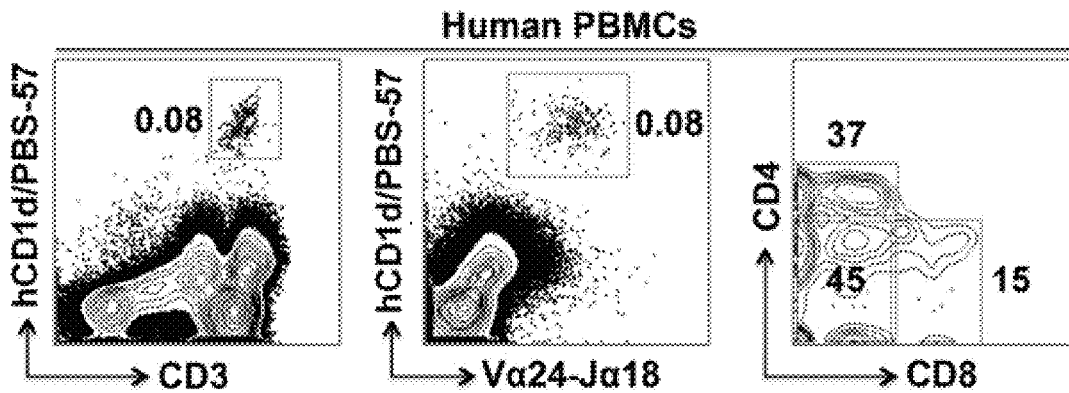
Figure 7B:
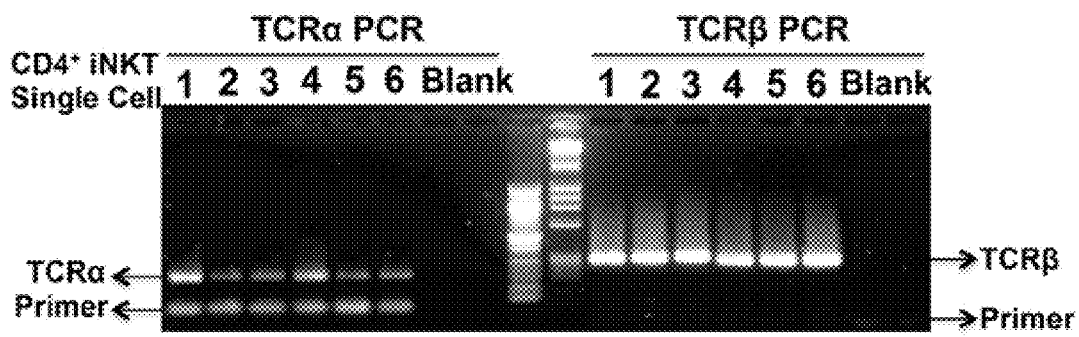
Figure 7C:
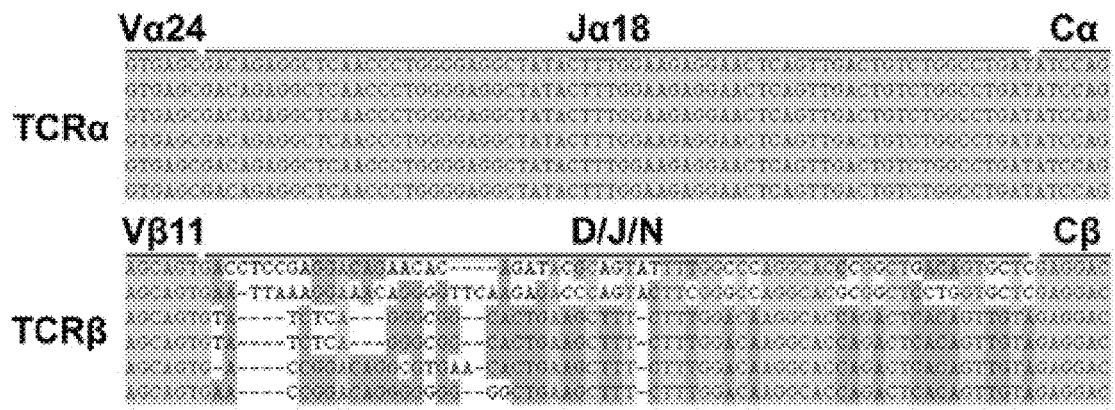

FIGS. 7A-7C schematically show the cloning of human iNKT TCR genes.

FIG. 7A shows flow cytometry analysis to detect human iNKT cells (gated as CD3$^{lo}$hCD1d/PBS-57$^+$Vα24-Jα18$^+$) and their CD4/CD8/DN subsets (gated as CD4$^+$CD8$^-$, CD4$^-$CD8$^+$ or CD4$^-$CD8$^-$, respectively) in PBMCs.

FIG. 7B is a gel image showing the TCRα and TCRβ PCR products from 6 CD4$^+$ iNKT single cells. Single-cell RT-PCR was to clone iNKT TCRs.

FIG. 7C show the sequencing results of the PCR products, showing an invariant TCRα (Vα24-Jα18) and semi-invariant TCRβ (Vβ11 joined with varied D/J/N segments). The top 6 sequences for iNKT TCRα are SEQ ID NO: 7, and for the iNKT TCR β sequences (the bottom 6 sequences), from top to bottom, the SEQ ID NOs are: SEQ ID NO: 8, SEQ ID NO: 9, SEQ ID NO: 10, SEQ ID NO: 11, SEQ ID NO: 12, and SEQ ID NO: 13.

Figure 8A:
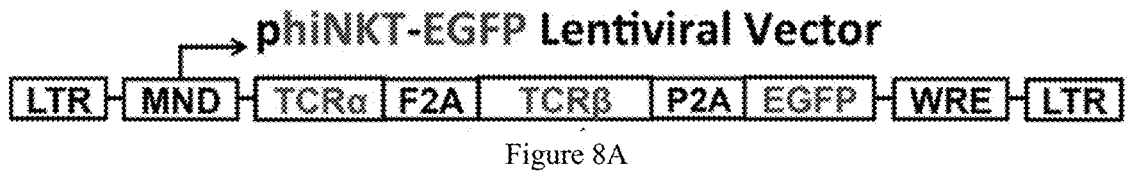
Figure 8B:
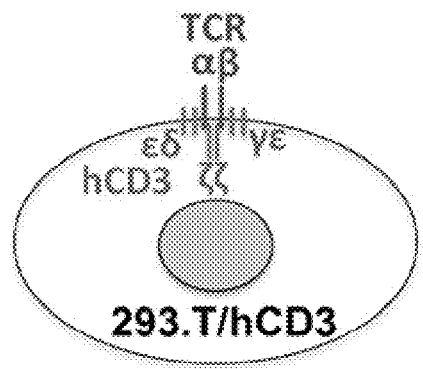
Figure 8C:
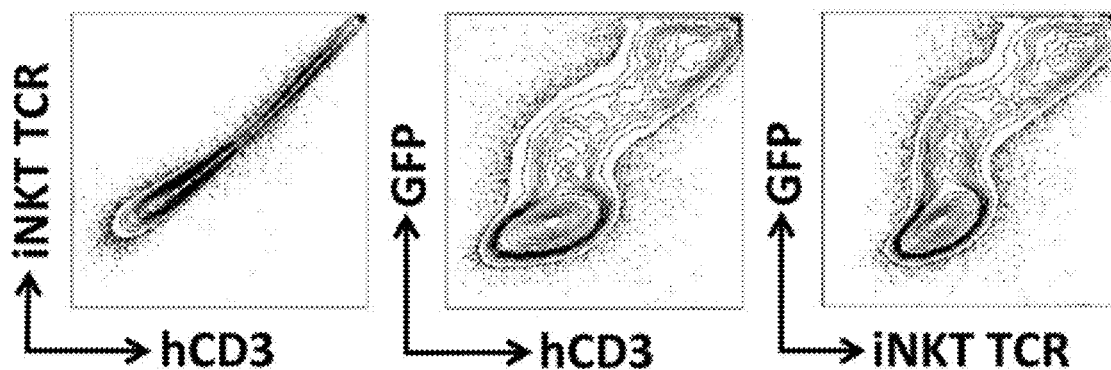

FIGS. 8A-8C schematically show the construction of human iNKT TCR delivery lentivectors. Construction of lentiviral vectors delivering human iNKT TCR genes.

FIG. 8A is a schematic representation of the phiNKT-EGFP lentivector. LTR: long-term repeats; MND: synthetic MND promoter; F2A: foot-and-mouth disease virus 2A sequence; P2A: porcine teschovirus-1 2A sequence; EGFP: enhanced green fluorescence protein; WRE: woodchuck responsive element.

FIG. 8B schematically shows the 293.T/hCD3 stable cell line used to test human TCR expression.

FIG. 8C shows flow cytometry analysis of GFP and surface expression of human iNKT TCRs in 293.T/hCD3 cells transduced with a representative phiNKT-EGFP lentivector.

Figure 9A:
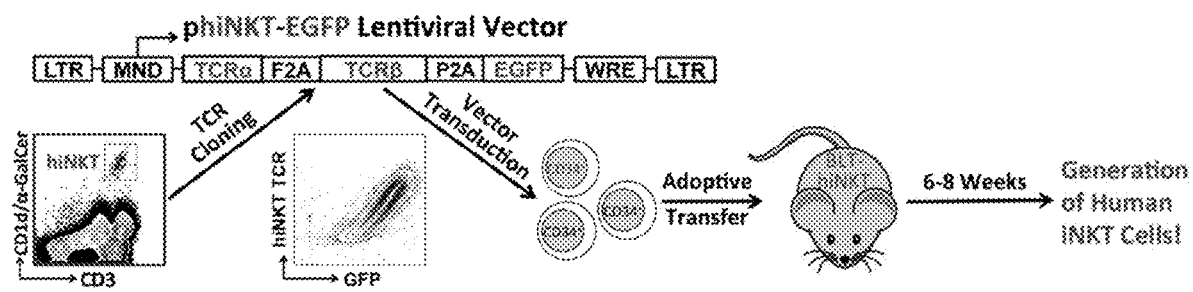
Figure 9B:
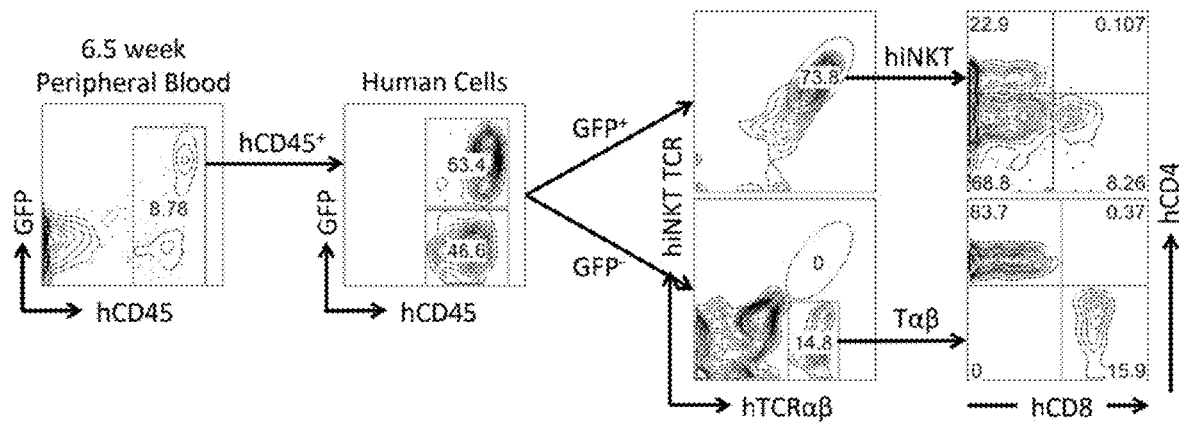

FIGS. 9A and 9B schematically show the generation of HSPC-iNKT cells and successful generation of HSPC-iNKT cells in BLT humanized mice.

FIG. 9A is a schematic of the experimental design to generate human HSPC-iNKT cells according to the present invention.

FIG. 9B show the successful detection of HSPC-iNKT cells in the peripheral blood of BLT-hiNKT mice 6.5 weeks post CD34$^+$ cell adoptive transfer.

DETAILED DESCRIPTION OF THE INVENTION

The present invention provides "HSPC-iNKT cells", invariant natural killer T (iNKT) cells engineered from hematopoietic stem cells (HSCs) and/or hematopoietic progenitor cells (HPCs), and methods of making and using thereof. As used herein, "HSPCs" is used to refer to HSCs, HPCs, or both HSCs and HPCs. The methods for making HSPC-iNKT cells according to the present invention are cost-effective and high-throughput. For example, using the methods of the present invention, one can readily implement retrovirus-transduced bone marrow transfer and generate HSPC-iNKT cells within as few as 6 weeks.

As disclosed herein, large numbers of HSPC-iNKT cells were generated by transducing HSPCs with one or more nucleic acid sequences encoding iNKT T cell receptors (TCRs) and engrafting the TCR-transduced HSPCs in subjects. Once engrafted, the transduced cells follow a two-stage developmental path, first in thymus and then in the periphery, which resembles that of endogenous iNKT cells and results in functional HSPC-iNKT cells. When tested in a mouse melanoma lung metastasis model, the HSPC-iNKT cells effectively protected mice from tumor metastasis.

HSPC-iNKT cells according to the present invention can also be generated in vitro. For example, HSPCs can be transduced with one or more iNKT TCR nucleic acid sequences and cultured with OP9-DL1 or MS5-DL4 stromal cells (Sun, et al. (2015) Cytokine 72:48-57) to result in TCR-engineered iNKT cells. The resulting iNKT cells can be further expanded by secondary culture with irradiated donor peripheral blood mononuclear cells (PBMCs) as antigen-presenting cells (APCs) or CD1d-expressing artificial antigen-presenting cells (aAPCs) in the presence of agonist antigen like α-galactosylceramide (α-GalCer). An example of such aAPCs could be K562 cells engineered to overexpress CD1d (Tian, et al. (2013) J. Immunol. 190:45.3).

As disclosed herein, HSPC-iNKT cells according to the present invention follow a classical iNKT cell development path, Check Point 1 in the thymus to gain iNKT TCR expression and Check Point 2 in the periphery to gain NK1.1 expression. They also display a typical iNKT cell phenotype (TCRβ$^{lo}$mCD1d/PBS-57$^{hi}$NK1.1$^{hi}$CD62L$^{lo}$CD44$^{hi}$CD4$^{+/-}$CD8$^-$) and exhibit full iNKT cell functionality with potent and fast response to antigen stimulation, both in vitro and in vivo. Thus, the HSPC-iNKT cells according to the present invention are functional, which means the HSPC-iNKT cells are able to produce, upon activation, one or more cytokines and/or chemokines such as IFNγ, TNFα, TGFβ, GM-CSF, IL-2, IL-4, IL-5, IL-6, IL-10, IL-13, IL-17, IL-21, RANTES, Eotaxin, MIP-1α, MIP-1β, and the like.

Because the HSPC-iNKT cells of the present invention are functional, they can be used to study iNKT cell biology. The development and function of HSPC-iNKT cells in healthy and disease conditions can be monitored by varying the levels of HSPC-iNKT cells in subjects. In addition, using the methods of the present invention, one can generate large numbers of clonal HSPC-iNKT cells and thereby investigate the similarities and differences between individual iNKT cell clones. For example, by studying the antigen recognition and functional differentiation of single iNKT cell clones, important clues might be revealed to increase understanding of the origins of various iNKT cell subsets with distinct functions, such as those iNKT cell subsets biased to produce Th1, Th2, or Th17 effector cytokines. The flexibility of the inventive methods also allow the convenient generation of HSPC-iNKT cells of different genomic backgrounds at a fast pace and an affordable cost, allowing examination of the functions of designated genes for regulating iNKT cell biology.

HSPC-iNKT cells according to the present invention can be used in a variety of therapeutic treatments. Unlike transgenic mouse technologies, the inventive methods can be applied to humans through gene-modified CD34$^+$ cell transfer and therefore can be used as therapeutics to treat a wide variety of diseases and disorders in humans. In addition, unlike iPS-derived iNKT cells, HSPC-iNKT cells according to the present invention do not contain exogenous oncogenes, such as Oct4, Sox2, Klf4, and c-Myc. Consequently, HSPC-iNKT cells of the present invention do not pose the same risks as iPS-derived iNKT cells when used to treat subjects. Therefore, the methods and HSPC-iNKT cells of the present invention can be used to provide subjects with a lifelong supply of iNKT cells. HSPC-iNKT cells according to the present invention can be used to treat various cancers such as melanoma, kidney cancer, lung cancer, prostate cancer, breast cancer, lymphoma, leukemia, and hematological malignancies, bacterial and viral infections such as tuberculosis, HIV, hepatitis, allergies such as asthma and eczema, and autoimmune diseases such as Type I diabetes, multiple sclerosis, and arthritis.

Donor HSPCs can be obtained from the bone marrow, peripheral blood, amniotic fluid, or umbilical cord blood of a donor. The donor can be an autologous donor, i.e., the subject to be treated with the HSPC-iNKT cells, or an allogenic donor, i.e., a donor who is different from the subject to be treated with the HSPC-iNKT cells. In embodiments where the donor is an allogenic donor, the tissue (HLA) type of the allogenic donor preferably matches that of the subject being treated with the HSPC-iNKT cells derived from the donor HSPCs.

According to the present invention, an HSPC is transduced with one or more exogenous iNKT TCR nucleic acid molecules. As used herein, an "iNKT TCR nucleic acid molecule" is a nucleic acid molecule that encodes an alpha chain of an iNKT T cell receptor (TCRα), a beta chain of an iNKT T cell receptor (TCRβ), or both. As used herein, an "iNKT T cell receptor" is one that is expressed in an iNKT cell and recognizes α-GalCer presented on CD1d. The TCRα and TCRβ sequences of iNKT TCRs can be cloned and/or recombinantly engineered using methods in the art. For example, an iNKT cell can be obtained from a donor and the TCR α and β genes of the iNKT cell can be cloned as described herein. The iNKT TCR to be cloned can be obtained from any mammalian including humans, non-human primates such monkeys, mice, rats, hamsters, guinea pigs, and other rodents, rabbits, cats, dogs, horses, bovines, sheep, goat, pigs, and the like. In some embodiments, the iNKT TCR to be cloned is a human iNKT TCR. In some embodiments, the iNKT TCR clone comprises human iNKT TCR sequences and non-human iNKT TCR sequences.

In some embodiments, the cloned TCR can have a TCRα chain from one iNKT cell and a TCRβ chain from a different iNKT cell. In some embodiments, the iNKT cell from which the TCRα chain is obtained and the iNKT cell from which the TCRβ chain is obtained are from the same donor. In some embodiments, the donor of the iNKT cell from which the TCRα chain is obtained is different from the donor of the iNKT cell from which the TCRβ chain is obtained. In some embodiments, the sequence encoding the TCRα chain and/or the sequence encoding the TCRβ chain of a TCR clone is modified. In some embodiments, the modified sequence may encode the same polypeptide sequence as the unmodified TCR clone, e.g., the sequence is codon optimized for expression. In some embodiments, the modified sequence may encode a polypeptide that has a sequence that is different from the unmodified TCR clone, e.g., the modified sequence encodes a polypeptide sequence having one or more amino acid substitutions, deletions, and/or truncations.

The cloned and/or recombinantly engineered iNKT TCRα and TCRβ chains are then inserted into one or more expression vectors to give TCR expression vectors. In some embodiments, the cloned and/or recombinantly engineered iNKT TCRα and TCRβ chains are provided in the same expression vector and are functionally linked to result in their co-expression. In some embodiments, the expression vector is a retroviral vector or a lentiviral vector.

The donor HSPCs are then transduced with one or more TCR expression vectors. In some embodiments, an HSPC is transduced with a first TCR expression vector that encodes an iNKT TCRα chain and a second TCR expression vector that encodes a TCRβ chain. In some embodiments, an HSPC is transduced with a TCR expression vector that encodes both an iNKT TCRα chain and an iNKT TCRβ chain. In some embodiments, expression of the iNKT TCRα chain and the iNKT TCRβ chain are under the same promotor in one TCR expression vector. In some embodiments, expression of the iNKT TCRα chain is under a first promotor and the expression of the iNKT TCRβ chain is under a second promotor in one TCR expression vector. In some embodiments, the TCR-transduced HSPCs are expanded in vitro. In some embodiments, the TCR-transduced HSPCs are engrafted in a subject to generate clonal populations of HSPC-iNKT cells. In some embodiments, the subject is in need of treatment with iNKT cells. As used herein, a subject "in need of" treatment with iNKT cells is one who suffers from a condition that may be treated, reduced, or alleviated by increasing the number of iNKT cells in the subject. Examples of such conditions include cancers such as melanoma, kidney cancer, lung cancer, prostate cancer, breast cancer, lymphoma, leukemia, and hematological malignancies, bacterial infections such as tuberculosis, viral infections such as HIV and hepatitis, and allergies and autoimmune diseases such as asthma, eczema, Type I diabetes, multiple sclerosis, and arthritis. In some embodiments, the subject is a host subject having thymus tissue suitable for thymic development of the TCR-transduced HSPCs into HSPC-iNKT cells. In some embodiments, the host subject is a BLT mouse, e.g., a mouse surgically implanted with human thymus tissue. In some embodiments, HSPC-iNKT cells are obtained from a host subject. In some embodiments, HSPC-iNKT cells obtained from a host subject are administered to a subject in need of treatment with iNKT cells.

In some embodiments, TCR-transduced HSPCs are cultured in vitro, e.g., with OP9-DL1 or MS5-DL4 stromal cells, to give rise to HSPC-iNKT cells, which are capable of expressing one or more cytokines and/or chemokines upon activation. These engineered iNKT cells can be administered to a subject in need of treatment with iNKT cells. In some embodiments, these engineered iNKT cells can be further expanded by secondary culture with irradiated donor PBMCs as antigen-presenting cells (APCs) or CD1d-expressing artificial antigen-presenting cells (aAPCs) in the presence of agonist antigen like α-GalCer, which can then be administered to a subject in need of treatment with iNKT cells.

In some embodiments, the HSPC-iNKT cells are activated ex vivo for utilization as, for example, a source of active iNKT cells for immunotherapy. Therefore, in some embodiments, the present invention is directed to methods for generating active HSPC-iNKT cells by contacting HSPC-iNKT cells with anti-CD3/CD28, PMA/Ionomycin, or α-GalCer presented by cells such as PBMCs, dendritic cells (DCs), and artificial APCs. When the DC-activated HSPC-iNKT cells are intended to be administered to humans, the α-GalCer used to pulse DCs is desirably of GMP grade. Pulsation of DCs with α-GalCer can be performed by methods in the art; for example, the pulsation can be performed by culturing the DCs in a serum-containing medium (for example, 10% FCS-containing RPMI-1640 medium and the like) containing α-GalCer at a concentration of about 0.01 to about 5 µg/mL for about 2 to about 48 hours. In some embodiments, the pulsation with α-GalCer may be performed by adding α-GalCer to the medium in the process of culturing and maturing the immature DC in the presence of GM-CSF (and IL-4), or post DC maturation induced by LPS-treatment. In some embodiments, the pulsation may be performed by adding α-GalCer to the medium in the step of co-culturing the DC matured as described below with HSPC-iNKT cells. As used herein, an "active" or "activated" HSPC-iNKT cell refers to a HSPC-iNKT cell that at least produces a Th1 cytokine such as IFN-γ in response to α-GalCer-presenting DC. The cell may further be capable of producing a Th2 cytokine such as IL-4 and/or be capable of proliferating.

TCR-transduced HSPCs and/or HSPC-iNKT cells according to the present invention may be locally or systemically administered to subjects. In some embodiments, the present invention provides compositions comprising TCR-transduced HSPCs and/or HSPC-iNKT cells according to the present invention. In some embodiments, the compositions comprising TCR-transduced HSPCs and/or HSPC-iNKT cells according to the present invention are formulated for injection, suspension, or drip infusion, by being blended with a pharmaceutically acceptable carrier. In some embodiments, the compositions of the present invention comprise TCR-transduced HSPCs and/or HSPC-iNKT cells suspended in a pharmaceutically acceptable carrier at a concentration of about $1.0 \times 10^5$ to $1.0 \times 10^7$ cells/ml. The term "pharmaceutically acceptable carrier" as used herein refers to a carrier or diluent, which are added to a composition by the hand of a human, which is generally non-toxic to an intended recipient, does not significantly inhibit the activity of the TCR-transduced HSPCs and/or HSPC-iNKT cells, and is not cytotoxic to the TCR-transduced HSPCs and/or HSPC-iNKT cells. Pharmaceutically acceptable carriers include physiological saline and isotonic solutions containing glucose or another auxiliary drug (e.g., D-sorbitol, D-mannitol, sodium chloride and the like). In some embodiments, compositions according to the present invention may include one or more excipients, diluents, auxiliaries, preservatives, solubilizing agents, buffers, thickening agents, gelling agents, foaming agents, surfactants, binders, suspending agents, disintegrating agents, wetting agents, solvents, plasticizers, fillers, colorants, dispersants, and the like. In some embodiments, the compositions further comprise an agent that activates the HSPC-iNKT cells, e.g., α-GalCer or salts or esters thereof, α-GalCer-presenting dendritic cells, or artificial APCs.

In some embodiments, a therapeutically effective amount of one or more of the TCR-transduced HSPCs and/or HSPC-iNKT cells according to the present invention are administered to a subject. The term "therapeutically effective amount" as used herein is intended to mean an amount which is effective to alleviate, ameliorate, or prevent a symptom or sign of a disease or condition to be treated.

The amount of a composition of the present invention administered to a subject and the route of administration depends on factors such as the severity of an infection affecting the subject, the activity and rate of clearance/proliferation of the TCR-transduced HSPCs and/or HSPC-iNKT cells, and the general physical characteristics of the subject including age, gender, and body weight. One of skill in the art may readily determine a therapeutically effective amount and route of administration in view of these and other considerations typical in medical practice. Therapeutically effective amounts of one or more TCR-transduced HSPCs and/or HSPC-iNKT cells according to the present invention may be readily determined by those skilled in the art without undue experimentation.

In general, a therapeutically effective amount of one or more TCR-transduced HSPCs and/or HSPC-iNKT cells is about $10^7$ to about $10^9$ cells per kg body weight of the subject being treated. A therapeutically effective amount of one or more TCR-transduced HSPCs and/or HSPC-iNKT cells according to the present invention may be manufactured and/or administered in single or multiple unit dose forms. In some embodiments, the one or more TCR-transduced HSPCs and/or HSPC-iNKT cells are provided as a composition having a concentration of about $1.0 \times 10^5$ to about $1.0 \times 10^7$ cells/ml of a pharmaceutically acceptable carrier or diluent. In some embodiments, the composition comprises about $1 \times 10^7$ to about $1 \times 10^9$ of the one or more TCR-transduced HSPCs and/or HSPC-iNKT cells. In some embodiments, the composition comprises about $1 \times 10^7$ to about $1 \times 10^8$ of the one or more TCR-transduced HSPCs and/or HSPC-iNKT cells. In some embodiments, the composition comprises about $1 \times 10^8$ to about $1 \times 10^9$ of the one or more TCR-transduced HSPCs and/or HSPC-iNKT cells. In some embodiments, a subject is administered an agent that activates the HSPC-iNKT cells, e.g., α-GalCer or salts or esters thereof, α-GalCer-presenting dendritic cells before, during, and/or after administration of the one or more TCR-transduced HSPCs and/or HSPC-iNKT cells.

The following examples are intended to illustrate but not to limit the invention.

EXAMPLES

Cloning of iNKT TCR Genes and Construction of Retroviral Delivery Vectors

Disclosed herein is a robust and high-throughput single-cell TCR cloning method for obtaining iNKT TCR genes. Briefly, single iNKT cells were sorted from mouse spleen cells using flow cytometry based on a stringent collection of surface markers gated as $CD3^{lo}$mCD1d/PBS-57$^+$TCR Vβ8$^+$ NK1.1$^+$ (See FIG. 1A). mCD1d/PBS-57 is the tetramer reagent that specifically identifies iNKT TCRs. TCR Vβ8 staining was used to focus on the dominant Vβ8$^+$ population of mouse iNKT cells. The sorted single iNKT cells were then subjected to TCR cloning (See FIG. 1B). Several verified iNKT TCR α and β pairs were inserted into the murine stem cell virus (MSCV)-based retroviral vector to yield TCR gene delivery vectors (See FIG. 1C and FIG. 1D). Their vector-mediated expressions were then tested in 293.T/mCD3, a stable cell line engineered to express mouse CD3 molecules that support the surface display of mouse TCRs (See FIG. 1E). One vector, which mediated high expression of a high-affinity iNKT TCR, was selected for the follow-up studies and was denoted as the miNKT vector (See FIG. 1D and FIG. 1F). The control MIG vector that encodes an EGFP reporter gene was denoted as the Mock vector (See FIG. 1D and FIG. 1F).

Generation of Clonal HSPC-iNKT Cells Through Genetic Engineering of HSPCs miNKT-transduced bone marrow transfer in B6 mice was performed to generate the recipient mice denoted as B6-miNKT (See FIG. 2A). In brief, HSPC-enriched bone marrow cells harvested from donor B6 mice were cultured in vitro, transduced with either Mock or miNKT retroviral vectors, then separately transferred into irradiated recipient B6 mice. The recipient mice were allowed to reconstitute their immune system over the course of 6-8 weeks, followed by analysis to determine the presence of HSPC-iNKT cells. Desirable titers of the newly constructed miNKT retroviral vector, e.g., about 0.5-1×10⁶ infectious units (IFU)/mL (FIG. 5) were obtained and high efficiencies of HSPC transduction (routinely over about 50% of the cultured bone marrow cells) were achieved. Compared with the Mock-engineered recipient mice, denoted as B6-Mock, a significant increase of iNKT cells was observed in the B6-miNKT mice from thymus to peripheral tissues, suggesting the successful generation of HSPC-iNKT cells (See FIG. 2B and FIG. 2C). Through titrating the miNKT vector-transduced HSPCs used for bone marrow transfer, the increase of the iNKT cells from as high as 50% of the total αβ T cells, down to a desired level in the B6-miNKT mice was controlled (See FIG. 2D and FIG. 2E). The ability to regulate the number of HSPC-iNKT cells can be valuable for clinical applications of this HSPC-engineered iNKT cell strategy. Study of the HSPC-iNKT cells from the B6-miNKT mice revealed that these iNKT cells displayed a typical phenotype of mouse iNKT cells in that they exhibited high expression of the NK1.1 marker, as well as a memory T-cell signature ($CD62L^{lo}CD44^{hi}$) and a $CD4^+CD8^-$ or $CD4^-CD8^-$ co-receptor expression pattern (See FIG. 2F). Almost all of these HSPC-iNKT cells showed positive staining for TCR Vβ8, indicating that they expressed the transgenic clonal iNKT TCR and suggesting that they were derived from the miNKT-engineered HSPCs (See FIG. 2F). The production of high levels of HSPC-iNKT cells in the B6-miNKT mice persisted for up to 6 months following the initial bone marrow transfer and also post-secondary bone marrow transfer, highlighting the long-term effectiveness of this HSPC-engineered iNKT cell strategy (See FIG. 2G and FIG. 2H).

Functionality of HSPC-iNKT Cells

Then the functionality of the HSPC-iNKT cells was analyzed. When stimulated with α-GalCer in vitro, the HSPC-iNKT cells proliferated vigorously by over 20-fold in 5 days and produced large amounts of the effector cytokines IFN-γ and IL-4 (See FIGS. 2I-2K). When B6-miNKT mice were immunized with bone marrow-derived dendritic cells (BMDCs) loaded with α-GalCer, the HSPC-iNKT cells mounted a strong and rapid response in vivo, expanding close to 20-fold in 3 days (See FIG. 2L). Notably, the in vivo expansion of these cells peaked at day 3 post-immunization, compared with 7 days post-immunization for conventional αβ T cells. This speedy in vivo response is a signature of the HSPC-iNKT cells. These results indicate that the HSPC-iNKT cells are fully functional.

Development of HSPC-iNKT Cells

Next, the development of the HSPC-iNKT cells was analyzed. iNKT cell progenitors gated as $TCRβ^{lo}mCD1d/PBS-57^+$ were detected in the thymus of the B6-miNKT mice and were found to follow a classic developmental path similar to that observed for endogenous iNKT progenitor cells in the control B6-Mock mice (See FIGS. 3A-3E). These progenitor cells appeared as $CD4^-CD8^-$ (DN), $CD4^+CD8^+$ (DP), and $CD4^+CD8^-$ (CD4 SP), corresponding with an iNKT development from DN to DP, then to CD4 SP or back to DN cells (See FIG. 3A). The expression of CD24, CD44, and DX5 markers on iNKT progenitor cells further defined their development in thymus into four stages: Stage 1 ($CD24^+CD44^-DX5^-$), Stage 2 ($CD24^-CD44^-DX5^-$), Stage 3 ($CD24^-CD44^+DX5^-$), and Stage 4 ($CD24^-CD44^+DX5^+$). Similar to their endogenous counterparts, TCR-transduced HSPC progenitors detected in the thymus of B6-miNKT mice followed a developmental path from Stages 1-4 (See FIG. 3B). In addition to their development in thymus to gain TCR expression (Control Point 1), iNKT cells also differ from conventional αβ T cells in that they need to undergo an additional maturation step in the periphery to acquire the expression of NK1.1 (Control Point 2). In B6-miNKT mice, HSPC-iNKT cells detected in the periphery did up-regulate NK1.1 expression compared with HSPC-iNKT cells detected in the thymus, similar to that observed for endogenous iNKT cells in the control B6-Mock mice (See FIG. 3C).

Overexpression of pre-rearranged αβ TCR genes in HSPCs has been shown to induce allelic exclusion and block the rearrangements of endogenous TCR genes in the resulting conventional αβ T cells. Study of the HSPC-iNKT cells generated in the B6-miNKT mice revealed that these cells expressed the transgenic TCR (Vβ8⁺), but not the other TCR Vβ chains analyzed in the experiment (See FIG. 3D and FIG. 3E). In particular, these HSPC-iNKT cells did not express the TCR Vβ7 used by about 10% of endogenous iNKT cells (See FIG. 3D and FIG. 3E). Analysis of TCR α chain expression also showed an exclusion of other TCR Vα expression on the HSPC-iNKT cells (See FIG. 3D). These results suggest that the HSPC-iNKT cells give rise to clonal iNKT cells that express the transgenic iNKT TCRs, likely through an allelic exclusion mechanism during iNKT cell development in thymus.

The lineage differentiation of HSPC-iNKT cells was also studied. By detecting intracellular expression of transgenic iNKT TCRs (gated as $Vβ8^{intra+}$), TCR-transduced HSPCs and their progeny cells could be tracked (See FIG. 6A and FIG. 6B). Notably, because only T cells express the CD3 molecules that support the surface display of TCRs and their signaling, the other cells that lack CD3 molecules can only express the transgenic iNKT TCRs intracellularly, and these TCRs are not functional. In addition to generating iNKT cells, these results show that TCR-transduced HSPCs can also differentiate into all other blood cell lineages analyzed, including B cells (gated as CD19⁺), macrophages (gated as $CD3^-CD19^-F4/80^+$), myeloid cells (gated as $CD3^-CD19^-CD11b^+$), and granulocytes (gated as $CD3^-CD19^-Gr-1^+$) (See FIG. 6A and FIG. 6B).

Antitumor Capacity of HSPC-iNKT Cells

The cancer therapy potential of the HSPC-iNKT cells was then studied. B6-miNKT mice and control B6-Mock mice were challenged with B16.F10 melanoma cells through i.v. injections and analyzed for lung metastasis 2 weeks later (See FIG. 4A). Experimental mice received immunization with either unloaded or α-GalCer-loaded BMDCs (denoted as BMDC/none or BMDC/α-GalCer, respectively) on Day 3 post tumor challenge to boost iNKT cell activities and to mimic a therapeutic vaccination treatment (See FIG. 4A). Monitoring of the HSPC-iNKT cells in the B6-miNKT mice showed that these cells actively responded to tumor challenge, evidenced by their expansion from about 1.5% to about 7% in blood (See FIG. 4B). In comparison, endogenous iNKT cells in the control B6-Mock mice also responded to tumor challenge, but their limiting starting number (<0.2%) only allowed them to reach about 1.7% in blood (See FIG. 4B). A significant protection from lung metastasis was observed in the B6-miNKT mice compared with that in the control B6-Mock mice, as evidenced by the reduction of both the number and size of tumor nodules (See FIGS. 4C-4E). Inclusion of a BMDC/α-GalCer immunization further expanded the HSPC-iNKT cells (up to about 30% in blood) (See FIG. 4B). However, no significant further reduction of lung tumor nodules was observed (See FIG. 4C), which may be due to a "saturation" of the antitumor capacity of iNKT cell-induced effector cells like NK cells and tumor-specific conventional αβ T cells that were limiting in mice. Total clearance of tumor metastasis likely requires combination therapy such as combining with adoptive transfer of additional effector cells. Notably, depigmentation of tumor nodules was observed in high numbers in the B6-iNKT mice (See FIG. 4F). Key molecules in the pigment synthesis pathway are a major class of tumor antigens for melanoma, and mutating or down-regulating these molecules are common strategies by which melanoma tumor cells escape immune attack, often leading to depigmentation. The presence of a large fraction of depigmented tumor nodules in the B6-miNKT mice therefore suggests a strong immune response against these tumors, presumably induced by the HSPC-iNKT cells through activation of antitumor NK and conventional αβ T cells (See FIG. 4F).

Human HSPC-iNKT Cells

Human HSPC-iNKT cells were successfully generated in BLT mice. Briefly, human iNKT TCR genes were cloned and inserted into an expression vector. Then human fetal liver CD34+ HSPCs were transduced with the TCR expression vector and transplanted into NOD/SCID/IL-2rγ−/− mice that were pre-implanted with human fetal liver and thymus. Two to three months later, clonal human HSPC-iNKT cells were generated in the BLT mice. Thus, the present invention can be used to generate human HSPC-iNKT cells for cell therapies.

The following examples are intended to illustrate but not to limit the invention.

MATERIALS AND METHODS

Mice and Materials

C57BL/6J (B6) mice were purchased from the Jackson Laboratory. Six- to ten-week-old females were used for all experiments unless otherwise indicated. All animal experiments were approved by the Institutional Animal Care and Use Committee of the University of California, Los Angeles.

α-Galactosylceramide (α-GalCer, KRN7000) was purchased from Avanti Polar Lipids; lipopolysaccharides (LPS) and 5-fluorouracil (5-FU) from Sigma; recombinant murine IL-3, IL-6 and stem cell factor (SCF) from PeproTech; and polybrene from Millipore. Fluorochrome-conjugated mCD1d/PBS-57 tetramer reagents were provided by the NIH Tetramer Core Facility (Emory University, Atlanta, GA). Fixable Viability Dye eFluor455UV was purchased from Affymetrix eBioscience.

Antibodies and Flow Cytometry

Fluorochrome-conjugated antibodies specific for mouse CD3, CD4, CD8, CD19, CD11b, CD24, CD62L, CD44, DX5, F4/80, Gr-1, TCRβ, TCR Vβ7, TCR Vβ8, and TCR Vα8.3 were purchased from BioLegend; for mouse NK1.1, IFN-γ, IL-4, TCR Vα2, TCR Vα3.2, TCR Vβ3, TCR Vβ4, TCR Vβ5, TCR Vβ6, TCR Vβ11, and TCR Vβ13, from BD Biosciences. Fc Block (anti-mouse CD16/32) was purchased from BD Biosciences. Cells were stained as previously described (Yang & Baltimore (2005) PNAS USA 102(12): 4518-4523) and analyzed using an LSRFortessa flow cytometer (BD Biosciences). FlowJo software was used to analyze the data.

ELISA

The ELISAs for detecting mouse cytokines were performed following a standard protocol from BD Biosciences. The capture and biotinylated antibody pairs for detecting mouse IFN-γ and IL-4 were also purchased from BD Biosciences. The streptavidin-HRP conjugate and mouse IFN-γ and IL-4 Single-Use ELISA Ready-Set-Go (RSG) Standards were purchased from Affymetrix eBioscience. The 3,3',5,5'-Tetramethylbenzidine (TMB) substrate was purchased from KPL. The samples were analyzed for absorbance at 450 nm using an Infinite M1000 microplate reader (Tecan).

Single-Cell iNKT TCR Cloning

The single-cell iNKT TCR RT-PCR was performed based on an established protocol (Smith, et al. (2009) Nat Protoc 4(3):372-384), with certain modifications. iNKT cells were sorted from mouse spleen cells based on a stringent forum of surface markers (CD3$^{lo}$mCD1d/PBS-57+TCR Vβ8+ NK1.1$^{hi}$) using a FACSAria II flow cytometer (BD Biosciences) (lo, low; hi, high). Single cells were sorted directly into PCR plates containing cell lysis buffer. The plates were then immediately flash frozen and stored at −80° C. until use. Upon thawing, the cell lysate from each cell was split in half on the same PCR plate and processed directly into iNKT TCR cloning for both α and β chain genes using a OneStep RTPCR kit (QIAGEN), following the manufacturer's instructions and using the iNKT TCR gene-specific primers. These primers were designed to amplify the ~200 bps spanning the CDR3 regions of the iNKT TCR α and β chain cDNAs and were customer-synthesized by Integrated DNA Technologies (IDT): for TCRα (forward primer: 5'-GGG AGA TAC TCA GCA ACT CTG GAT AAA GAT GC-3' (SEQ ID NO: 14); reverse primer: 5'-CCA GAT TCC ATG GTT TTC GGC ACA TTG-3' (SEQ ID NO: 15)) and for TCRβ (forward primer: 5'-GGA GAT ATC CCT GAT GGA TAC AAG GCC TCC-3' (SEQ ID NO: 16); reverse primer: 5'-GGG TAG CCT TTT GTT TGT TTG CAA TCT CTG-3' (SEQ ID NO: 17)). Verified sequences (productive germline Vα14-Jα18-Cα assembly for TCRα and Vβ8-D/J/N-Cβ assembly for TCRβ) were used to construct the complete cDNA sequences encoding the TCR α and β chains from a single cell, based on information about murine TCR genomic segments (the international ImMuno-GeneTics information system (IMGT), see WorldWideWebDOTimgtDOTorg, wherein "WorldWideWeb" is "www" and "DOT" is "."). The selected iNKT TCR α and β pair cDNAs were then synthesized as a single bicistronic gene, with codon optimization and a F2A sequence linking the TCRα and TCRβ cDNAs to enable their coexpression (GenScript).

The 293.T/mCD3 Stable Cell Line

HEK293.T human embryonic kidney epithelial cells (ATCC) were stably transduced with a lentiviral vector (Yang L, et al. (2008) Nat Biotechnol 26(3):326-334) co-expressing all four chains of mouse CD3 complex (CD3γ, CD3δ, CD3e, and CD3ζ), through linking the four cDNAs with three different 2A sequences (F2A, foot-and-mouth disease virus 2A; P2A, porcine teschovirus-1 2A; and T2A, Thosea asigna virus 2A). The transduced cells were then transiently transfected with an MOT1 vector encoding a mouse CD8 TCR, using a standard calcium precipitation procedure (Yang & Baltimore (2005) PNAS USA 102(12): 4518-4523). Single cells supporting the high surface expression of OT1 TCRs (gated as CD3+TCR Vβ5+) were sorted out using flow cytometry and grown into single-cell clones. A stable, single-cell clone, which lost OT1 TCR expression, but retained the capacity to support mouse TCR surface expression, was selected and designated as the 293.T/mCD3 stable cell line.

Mock and miNKT Retroviruses

Mock (MIG) retroviral vector was reported previously (Yang & Baltimore (2005) PNAS USA 102(12): 4518-4523). miNKT retroviral vector was constructed by inserting the synthetic bicistronic gene (iNKT TCRα-F2ATCRβ) into the MIG vector, replacing the IRES-EGFP segment. Retroviruses were made using HEK293.T cells, following a standard calcium precipitation protocol as previously described (Yang & Baltimore (2005) PNAS USA 102(12): 4518-4523).

HSPC Isolation, Transduction, Adoptive Transfer, and Secondary Bone Marrow Transfer The procedures were reported previously (Yang & Baltimore (2005) PNAS USA 102(12): 4518-4523). In brief, B6 mice were treated with 5-fluorouracil (250 μg per gram body weight). Five days later, bone marrow (BM) cells were harvested and cultured for 4 days in BM cell culture medium containing recombinant murine IL-3 (20 ng/mL), IL-6 (50 ng/mL), and SCF (50 ng/mL). On Days 2 and 3, BM cells were spin-infected with retroviruses supplemented with 8 μg/mL of polybrene, at 770×g, 30° C. for 90 minutes on Day 4, BM cells were collected and i.v. injected into B6 recipients that had received 1,200 rads of total body irradiation (about 1-2×$10^6$ transduced BM cells per recipient). For secondary BM transfer, fresh total BM cells harvested from the primary BM recipients were i.v. injected into secondary B6 recipient mice that had received 1,200 rads of total body irradiation (about 10×$10^6$ total BM cells per recipient). The BM recipient mice were maintained on the combined antibiotics sulfamethoxazole and trimethoprim oral suspension (Septra; Hi-Tech Pharmacal) in a sterile environment for 6-8 weeks until analysis or use for further experiments.

Bone Marrow Derived Dendritic Cell Generation, Antigen Loading, and Mouse Immunization B6 mouse BMDCs were generated from BM cell cultures and matured with LPS as described previously (Yang & Baltimore (2005) PNAS USA 102(12): 4518-4523). The LPS-matured BMDCs were then cultured at 37° C. in a 6-well plate at 10×$10^6$ cells/well/2 mL BMDC culture medium containing 5 μg/mL of α-GalCer for 2 hours, with gentle shaking every 30 minutes. The α-GalCer-loaded BMDCs were then washed twice with PBS and used to immunize mice through i.v. injection (about 1×$10^6$ BMDCs/mouse).

In Vitro iNKT Cell Functional Assays

Spleen cells containing iNKT cells were cultured in vitro in a 24-well plate at 2×$10^6$ cells per well in regular mouse lymphocyte culture medium, with or without the addition of α-GalCer (100 ng/mL), for 5 days. On Days 3 and 5, cells were collected and assayed for iNKT cell expansion using flow cytometry, and the cell culture supernatants were collected and assayed for effector cytokine (IFN-γ and IL-4) production by ELISA. On Day 3, some cells were also treated with 4 μL/6 mL BD GolgiStop for 4-6 hours and then assayed for intracellular cytokine production using flow cytometry via intracellular staining using the BD Cytofix/Cytoperm Fixation/Permeabilization Kit (BD Biosciences).

In Vivo iNKT Cell Functional Assay

Mice were immunized with α-GalCer-loaded BMDCs through i.v. injection (about 1×$10^6$ BMDCs per mouse) and then periodically bled to monitor the in vivo iNKT cell responses using flow cytometry.

B16 Melanoma Lung Metastasis Mouse Model

Mice that received i.v. injection of 0.5-1×$10^6$ B16.F10 melanoma cells were allowed to develop lung metastasis over the course of 2 weeks (Fujii S, et al. (2002) Nat Immunol 3(9):867-874). On day 3 post tumor challenge, the experimental mice received i.v. injection of 1×$10^6$ BMDCs that were either unloaded or loaded with α-GalCer. On Day 14, mice were euthanized, and their lungs were harvested and analyzed for melanoma metastasis by counting tumor nodules under a Zeiss Stemi 2000-CS microscope (Carl Zeiss AG) at 10× magnification. Representative lungs were also analyzed by immunohistology.

Immunohistology

Lung tissues collected from the experimental mice were fixed in 10% neutral-buffered formalin and embedded in paraffin for sectioning (5 μm thickness), followed by hematoxylin and eosin staining using standard procedures (UCLA Translational Pathology Core Laboratory, Los Angeles, CA). The sections were imaged using an Olympus BX51 upright microscope equipped with an Optronics Macrofire CCD camera (AU Optronics) at 40× and 100× magnifications. The images were analyzed using Optronics PictureFrame software (AU Optronics). Statistical analysis. Student's two-tailed t test was used for paired comparisons. Data are presented as mean±SEM, unless otherwise indicated. $P<0.01$ was considered significant.

Cloning of Human iNKT TCR Genes

Human iNKT TCR genes were cloned as above and with the following modifications. iNKT cells were sorted from fresh PBMCs of healthy human donors using flow cytometry based on a stringent forum of markers (gated as $CD161^+$ $CD3^+CD1d/α$-$GalCer^+Vα24$-$Jα18^+Vβ11^+$). Single iNKT cells were sorted directly into PCR plates containing cell lysis buffer. The cell lysate from each single cells was then split into half on the same PCR plate, and be processed directly into iNKT TCR cloning for both α and β chains using a OneStep RT-PCR kit (Qiagen) following the manufacturer's instructions, and using the gene-specific primers verified by the preliminary study. The PCR products were then examined by electrophoresis and the amplicons corresponding to iNKT TCR α and β chains were sequenced. For each single cell, verification that it expressed an invariant alpha chain (Vα24-Jα18-Cα) and a semi-invariant beta chain (Vβ11-D/J/N-Cβ) helped to certify its iNKT identity, as well as reveal its unique TCRβ D/J/N sequence, with which a unique "iNKT TCR clone" was established. This cloning strategy exemplified in FIGS. 7A-7C was high-throughput, and a large collection of TCR clones from each iNKT subset were generated.

Construction of Human iNKT TCR Delivery Lentivectors

Human iNKT TCR genes were cloned into a chosen lentivector to generate lentiviral vectors that co-deliver the iNKT TCR genes as well as an EGFP reporter gene, denoted as phiNKT-EGFP (FIG. 8A). To facilitate the evaluation of lentivector-mediated TCR expression, the human embryonic kidney epithelial cell line 293.T was engineered to stably express all four chains of human CD3 (EA), resulting in a 293.T/hCD3 cell line that allows for the surface display of human TCRs for their convenient detection (FIG. 8B). Transduction of the 293.T/hCD3 cells with the phiNKT-EGFP lentivectors revealed an efficient co-expression of the encoded human iNKT TCR genes and the EGFP report gene (FIG. 8C).

Generation of Human HSPC-iNKT Cells

Human fetal liver $CD34^+$ HSPCs were transduced with a selected phiNKT-EGFP lentivector. They were then transplanted into NOD/SCID/IL-2rγ$^{-/-}$ mice that were pre-implanted with human fetal liver and thymus, to generate iNKT TCR-engineered BLT mice (denoted as BLT-iNKT) following an established protocol. Two to three months later, the BLT mice were analyzed for the presence of human HSPC-iNKT cells (FIG. 9A). The data in FIG. 9B evidences that the methods of the present invention can be used to successfully generate clonal human HSPC-iNKT cells in iNKT TCR-engineered BLT mice.

iNKT TCR Sequences

Because invariant natural killer T (iNKT) cells express T cell receptors (TCRs) comprising the identical alpha chains and beta chains of limited diversity, the full sequence of one alpha chain is listed as being exemplary, however, other alpha chains can be implemented according to the present invention. Similarly, for the beta chains, the full sequence of one beta chain and the sequences of the diverse region (D/J/N region) of a variety of beta chains are listed for exemplary purposes, but other beta chains can be implemented according to the present invention. As an example, beta chains that utilize the human TCR V beta 11 segment were used. Therefore, the TCR beta V regions of these beta chains are identical, leaving the D/J/N segment the only diverse regions in these iNKT TCR beta chains. The genomic sequence, codon-optimized gene sequence and protein sequence of each iNKT TCR alpha and beta chains are listed below. Each unique D/J/N region makes a unique beta chain, which in combination with the identical alpha chain forms a unique iNKT TCR pair.

```
Human iNKT TCR Alpha Chain Full Sequence
(Identical for All Human iNKT TCRs)
cDNA Genomic Sequence (831 bp)
                                      (SEQ ID NO: 18)
atgaaaaagcatctgacgaccttcttggtgattttgtggctttatttt ataggggaatggcaaaaaccaagtggagcagagtcctcagtccctgat catcctggagggaaagaactgcactcttcaatgcaattatacagtgagc ccctt cagcaact taaggtggtataagcaagatactgggagaggtcctg tttccctgacaatcatgactttcagtgagaacacaaagtcgaacggaag atatacagcaactctggatgcagacacaaagcaaagctctctgcacatc acagcctcccagctcagcgattcagcctcctacatctgtgtggtgagcg acagaggctcaaccctggggaggctatactttggaagaggaactcagtt gactgtctggcctgatatccagaaccctgaccctgccgtgtaccagctg agagactctaaatccagtgacaagtctgtctgcctattaccgattttg attctcaaacaaatgtgtcacaaagtaaggattctgatgtgtatatcac agacaaaactgtgctagacatgaggtctatggacttcaagagcaacagt gctgtggcctggagcaacaaatctgactttgcatgtgcaaacgccttca caacagcattattccagaagacaccttcttccccagcccagaaagttc ctgtgatgtcaagctggtcgagaaaagctttgaaacagatacgaaccta aactttcaaaacctgtcagtgattgggttccgaatcctcctcctgaaag tggccgggtttaatctgctcatgacgctgcggctgtggtccagctga cDNA Codon-Optimized Sequence (831 bp)
                                      (SEQ ID NO: 19)
atgaaaaagcatctgacaacattcctggtcattctgtggctgtacttct accgaggcaacggcaaaaatcaggtggagcagtcccacagtccctgat cattctggagggaagaactgcactctgcagtgtaattcaccgtgtct cccttt agtaacctgcgctggtataaacaggacaccggacgaggacccg tgagcctgacaatcatgactttctcagagaacacaaagagcaatggacg gtacaccgctacactggacgcagataccaaacagagctccctgcacatc acagcatctcagctgtcagatagcgcctcctacatttgcgtggtctctg accgagggagtaccctgggccgactgtattttggaaggggacccagct gacagtgtggcccgacatccagaacccagatcccgccgtctaccagctg cgcgacagcaagtcagtgataaaagcgtgtgcctgttcacagactttg attctcagactaatgtctctcagagtaaggacagtgacgtgtacattac tgacaaaaccgtcctggatatgaggagcatggacttcaagtcaaacagc
``` gccgtggcttggtcaaacaagagcgacttcgcatgcgccaatgcttta acaattcaatcattccagaggataccttctttcctagcccagaatcaag ctgtgacgtgaagctggtcgagaaagtttcgaaactgataccaacctg aattttcagaacctgtctgtgatcggcttcagaatcctgctgctgaagg tcgccggctttaatctgctgatgacactgagactgtggtcctcttga

```
Protein Sequence (276 aa)
                                      (SEQ ID NO: 20)
MKKHLTTFLVILWLYFYRGNGKNQVEQSPQSLIILEGKNCTLQCNYTVS

PFSNLRWYKQDTGRGPVSLTIMTFSENTKSNGRYTATLDADTKQSSLHI

TASQLSDSASYICVVSDRGSTLGRLYFGRGTQLTVWPDIQNPDPAVYQL

RDSKSSDKSVCLFTDFDSQTNVSQSKDSDVYITDKTVLDMRSMDFKSNS

AVAWSNKSDFACANAFNNSIIPEDTFFPSPESSCDVKLVEKSFETDTNL

NFQNLSVIGFRILLLKVAGFNLLMTLRLWSS

Human iNKT TCR Beta Chain Full Sequence
(the D/J/N regions are in bold)
cDNA Genomic Sequence (870 bp + D/J/N)
                                      (SEQ ID NO: 21)
atgactatcaggctcctctgctacatgggcttttattttctgggggcag gcctcatggaagctgacatctaccagaccccaagataccttgttatagg gacaggaagaagatcactctggaatgttctcaaaccatgggccatgac aaaatgtactggtatcaacaagatccaggaatggaactacacctcatcc actattcctatggagttaattccacagagaagggagatctttcctctga gtcaacagtctccagaataaggacggagcattttcccctgaccctggag tctgccaggccctcacatacctctcagtacctctgtgccagc (D/J/N)

gaggacctgaacaaggtgttcccaccgaggtcgctgtgttgagccat cagaagcagagatctcccacacccaaaaggccacactggtgtgcctggc cacaggcttcttccctgaccacgtggagctgagctggtgggtgaatggg aaggaggtgcacagtggggtcagcacggaccgcagcccctcaaggagc agcccgccctcaatgactccagatactgcctgagcagccgcctgagggt ctcggccaccttctggcagaaccccgcaaccacttccgctgccaagtc cagttctacgggctctcggagaatgacgagtggaccaggatagggcca aaccgtcacccagatcgtcagcgccgaggcctggggtagagcagactg tggctttacctcggtgtcctaccagcaagggtcctgtctgccaccatc ctctatgagatcctgctagggaaggccaccctgtatgctgtgctggtca gcgcccttgtgttgatggccatggtcaagagaaaggatttctga cDNA Codon-Optimized Sequence (870 bp + D/J/N)
                                      (SEQ ID NO: 22)
atgaccatccggctgctgtgctacatgggcttctattttctgggggcag gcctgatgaagccgacatctaccagactcccagataccttggtcatcgg aaccgggaagaaaattacactggagtgttcccagacaatgggccacgat aagatgtactggtatcagcaggaccctgggatggaactgcacctgatcc attactcctatggcgtgaactctaccgagaagggcgacctgagcagcga atccaccgtctctcgaattaggacagagcactttcctctgactctggaa agcgcccgaccaagtcatacatcacagtacctgtgcgctagc (D/J/N)

-continued gaggacctgaataaggtgttcccccctgaggtggctgtctttgaaccaa gtgaggcagaaatttcacatacacagaaagccaccctggtgtgcctggc taccggcttctttcccgatcacgtggagctgagctggtgggtcaacggc aaggaagtgcatagcggagtctccacagacccacagcccctgaaagagc agcctgctctgaatgattccagatactgcctgtctagtagactgcggt gtctgccaccttctggcagaacccaaggaatcatttcagatgtcaggtg cagttttatggcctgagcgagaacgatgaatggactcaggacagggcta agccagtgacccagatcgtcagcgcagaggcctggggaagagcagactg cgggtttacaagcgtgagctatcagcagggcgtcctgagcgccacaatc ctgtacgaaattctgctgggaaaggccactctgtatgctgtgctggtct ccgctctggtgctgatggcaatggtcaagcggaaagatttctga Protein Sequence (289 aa + D/J/N)

(SEQ ID NO: 23)
MTIRLLCYMGFYFLGAGLMEADIYQTPRYLVIGTGKKITLECSQTMGHD

KMYWYQQDPGMELHLIHYSYGVNSTEKGDLSSESTVSRIRTEHFPLTLE

SARPSHTSQYLCAS (D/J/N) EDLNKVFPPEVAVFEPSEAEISHTQKAT

LVCLATGFFPDHVELSWWVNGKEVHSGVSTDPQPLKEQPALNDSRYCLS

SRLRVSATFWQNPRNHFRCQVQFYGLSENDEWTQDRAKPVTQIVSAEAW

GRADCGFTSVSYQQGVLSATILYEILLGKATLYAVLVSALVLMAMVKRK

DF

Human iNKT TCR Beta Chain Diverse Region
(D/J/N) Sequence
Human iNKT TCR Beta Chain Cloned from the
CD4+CD8- (CD4 SP) Subpopulation
cDNA Genomic Sequence (60 bp)

(SEQ ID NO: 24)
GTAGCGGTTGGGCCCCAAGAGACCCAGTACTTCGGGCCAGGCACGCGGC

TCCTGGTGCTC cDNA Codon-Optimized Sequence (60 bp)

(SEQ ID NO: 25)
GTGGCAGTCGGACCTCAGGAGACCCAGTACTTCGGACCCGGCACCCGCC

TGCTGGTGCTG

Protein Sequence (20 aa)

(SEQ ID NO: 26)
VAVGPQETQYFGPGTRLLVL

Human iNKT TCR Beta Chain Cloned from the
CD4+CD8- (CD4 SP) Subpopulation
cDNA Genomic Sequence (54 bp)

(SEQ ID NO: 27)
AGTGGGCCAGGGTACGAGCAGTACTTCGGGCCGGGCACCAGGCTCACGG

TCACA cDNA Codon-Optimized Sequence (54 bp)

(SEQ ID NO: 28)
TCAGGACCCGGCTACGAGCAGTATTTCGGCCCCGGAACTCGGCTGACCG

TGACC

Protein Sequence (18 aa)

(SEQ ID NO: 29)
SGPGYEQYFGPGTRLTVT

Human iNKT TCR Beta Chain Cloned from the
CD4+CD8- (CD4 SP) Subpopulation
cDNA Genomic Sequence (57 bp)

(SEQ ID NO: 30)
AGTCCCCAATTAAACACTGAAGCTTTCTTTGGACAAGGCACCAGACTCA

CAGTTGTA cDNA Codon-Optimized Sequence (57 bp)

(SEQ ID NO: 31)
TCTCCACAGCTGAACACCGAGGCCTTCTTCGGGCAGGGCACAAGGCTTA

CCGTGGTG

Protein Sequence (19 aa)

(SEQ ID NO: 32)
SPQLNTEAFFGQGTRLTVV

Human iNKT TCR Beta Chain Cloned from the
CD4+CD8- (CD4 SP) Subpopulation
cDNA Genomic Sequence (78 bp)

(SEQ ID NO: 33)
AGTGAATTGCGGGCGCTCGGGCCCAGCTCCTATAATTCACCCCTCCACT

TTGGGAACGGGACCAGGCTCACTGTGACA cDNA Codon-Optimized Sequence (78 bp)

(SEQ ID NO: 34)
TCCGAACTCCGAGCCCTGGGGCCTAGCTCCTACAATAGCCCCCTGCACT

TTGGCAACGGAACCAGGCTGACGGTCACC

Protein Sequence (26 aa)

(SEQ ID NO: 35)
SELRALGPSSYNSPLHFGNGTRLTVT

Human iNKT TCR Beta Chain Cloned from the
CD4+CD8- (CD4 SP) Subpopulation
cDNA Genomic Sequence (60 bp)

(SEQ ID NO: 36)
AGTGAACAGGGGACTACTGCGGGAGCTTTCTTTGGACAAGGCACCAGAC

TCACAGTTGTA cDNA Codon-Optimized Sequence (60 bp)

(SEQ ID NO: 37)
TCCGAACAGGGAACCACAGCAGGAGCCTTCTTCGGTCAGGGAACAAGAC

TGACAGTCGTG

Protein Sequence (20 aa)

(SEQ ID NO: 38)
SEQGTTAGAFFGQGTRLTVV

Human iNKT TCR Beta Chain Cloned from the
CD4-CD8+ (CD8 SP) Subpopulation
cDNA Genomic Sequence (66 bp)

(SEQ ID NO: 39)
AGTGAGTCACGACATGCGACAGGAAACACCATATATTTTGGAGAGGGAA

GTTGGCTCACTGTTGTA cDNA Codon-Optimized Sequence (66 bp)

(SEQ ID NO: 40)
AGCGAGAGCAGGCACGCAACCGGGAACACCATATACTTTGGCGAGGGCT

CCTGGCTGACTGTGGTG

Protein Sequence (22 aa)

(SEQ ID NO: 41)
SESRHATGNTIYFGEGSWLTVV

Human iNKT TCR Beta Chain Cloned from the
CD4-CD8+ (CD8 SP) Subpopulation
cDNA Genomic Sequence (69 bp)

(SEQ ID NO: 42)
AGTGTACCCGGGAACGACAGGGGCAATGAAAAACTGTTTTTTGGCAGTG

GAACCCAGCTCTCTGTCTTG cDNA Codon-Optimized Sequence (69 bp)
(SEQ ID NO: 43)
TCCGTGCCTGGCAACGATAGAGGTAACGAGAAGCTGTTTTTCGGATCCG

GCACACAGCTGTCTGTCCTG

Protein Sequence (23 aa)
(SEQ ID NO: 44)
SVPGNDRGNEKLFFGSGTQLSVL

Human iNKT TCR Beta Chain Cloned from the
CD4-CD8+ (CD8 SP) Subpopulation
cDNA Genomic Sequence (72 bp)
(SEQ ID NO: 45)
AGTGAAGGGGGGGGCCTTAAGCTAGCCAAAAACATTCAGTACTTCGGCG

CCGGGACCCGGCTCTCAGTGCTG cDNA Codon-Optimized Sequence (72 bp)
(SEQ ID NO: 46)
AGTGAGGGAGGGGGACTGAAGCTGGCTAAGAATATTCAGTACTTCGGCG

CCGGCACTAGACTGTCTGTGCTG

Protein Sequence (24 aa)
(SEQ ID NO: 47)
SEGGGLKLAKNIQYFGAGTRLSVL

Human iNKT TCR Beta Chain Cloned from the
CD4-CD8- (DN) Subpopulation
cDNA Genomic Sequence (69 bp)
(SEQ ID NO: 48)
AGTGAATTCGCCTCTTCGGTACGTGGAAACACCATATATTTTGGAGAGG

GAAGTTGGCTCACTGTTGTA cDNA Codon-Optimized Sequence (69 bp)
(SEQ ID NO: 49)
TCTGAGTTCGCGAGCAGCGTCCGGGGTAATACCATTTACTTCGGGGAAG

GCAGCTGGCTGACCGTGGTG

Protein Sequence (23 aa)
(SEQ ID NO: 50)
SEFASSVRGNTIYFGEGSWLTVV

Human iNKT TCR Beta Chain Cloned from the
CD4-CD8- (DN) Subpopulation
cDNA Genomic Sequence (60 bp)
(SEQ ID NO: 51)
AGTGCGGCATTAGGCCGGGAGACCCAGTACTTCGGGCCAGGCACGCGGC

TCCTGGTGCTC cDNA Codon-Optimized Sequence (60 bp)
(SEQ ID NO: 52)
TCTGCAGCCCTTGGCCGAGAGACTCAGTACTTCGGCCCTGGCACAAGAC

TGCTCGTGCTC

Protein Sequence (20 aa)
(SEQ ID NO: 53)
SAALGRETQYFGPGTRLLVL

Human iNKT TCR Beta Chain Cloned from the
CD4-CD8- (DN) Subpopulation
cDNA Genomic Sequence (63 bp)
(SEQ ID NO: 54)
AGTGCCTCCGGGGGTGAATCCTACGAGCAGTACTTCGGGCCGGGCACCA

GGCTCACGGTCACA cDNA Codon-Optimized Sequence (63 bp)
(SEQ ID NO: 55)
AGCGCCTCCGGAGGAGAGTCATACGAACAGTATTTCGGCCCTGGCACAC

GCCTCACTGTGACC

Protein Sequence (21 aa)
(SEQ ID NO: 56)
SASGGESYEQYFGPGTRLTVT

Human iNKT TCR Beta Chain Cloned from the
CD4-CD8- (DN) Subpopulation
cDNA Genomic Sequence (90 bp)
(SEQ ID NO: 57)
AGCGGTCGGGTCTCGGGGGGCGATTCCCTCATAGCGTTTCTAGGCCAAG

AGACCCAGTACTTCGGGCCAGGCACGCGGCTCCTGGTGCTC cDNA Codon-Optimized Sequence (90 bp)
(SEQ ID NO: 58)
TCAGGACGAGTGTCCGGAGGGGATAGCCTCATCGCATTTCTGGGGCAGG

AAACTCAGTACTTCGGACCCGGAACACGCCTCCTGGTGCTG

Protein Sequence (30 aa)
(SEQ ID NO: 59)
SGRVSGGDSLIAFLGQETQYFGPGTRLLVL

Human iNKT TCR Beta Chain Cloned from the
CD4-CD8- (DN) Subpopulation
cDNA Genomic Sequence (69 bp)
(SEQ ID NO: 60)
AGTGTACCCGGGAACGACAGGGGCAATGAAAAACTGTTTTTTGGCAGTG

GAACCCAGCTCTCTGTCTTG cDNA Codon-Optimized Sequence (69 bp)
(SEQ ID NO: 61)
TCCGTGCCTGGCAACGATAGAGGTAACGAGAAGCTGTTTTTCGGATCCG

GCACACAGCTGTCTGTCCTG

Protein Sequence (23 aa)
(SEQ ID NO: 62)
SVPGNDRGNEKLFFGSGTQLSVL

STATISTICAL ANALYSIS

Student's two-tailed t test was used for paired comparisons. Data are presented as mean±SEM, unless otherwise indicated. P<0.01 was considered significant.

To the extent necessary, the following are herein incorporated by reference:

Restifo, N. P., Dudley, M. E. & Rosenberg, S. A. Adoptive immunotherapy for cancer: harnessing the T cell response. Nat Rev Immunol 12, 269-281, doi:10.1038/nri3191 (2012).

Vivier, E., Ugolini, S., Blaise, D., Chabannon, C. & Brossay, L. Targeting natural killer cells and natural killer T cells in cancer. Nat Rev Immunol 12, 239-252, doi:10.1038/nri3174 (2012).

Berzins, S. P., Smyth, M. J. & Baxter, A. G. Presumed guilty: natural killer T cell defects and human disease. Nat Rev Immunol 11, 131-142, doi:10.1038/nri2904 (2011).

Bendelac, A., Savage, P. B. & Teyton, L. The biology of NKT cells. Annu Rev Immunol 25, 297-336, doi:10.1146/annurev.immunol.25.022106.141711 (2007).

Yang, L. & Baltimore, D. Long-term in vivo provision of antigen-specific T cell immunity by programming hematopoietic stem cells. PNAS USA 102, 4518-4523, doi:10.1073/pnas.0500600102 (2005).

Giannoni, F. et al. Allelic exclusion and peripheral reconstitution by TCR transgenic T cells arising from transduced human hematopoietic stem/progenitor cells. Molecular therapy: the journal of the American Society of Gene Therapy 21, 1044-1054, doi:10.1038/mt.2013.8 (2013).

Vatakis, D. N. et al. Antitumor activity from antigen-specific CD8 T cells generated in vivo from genetically engineered human hematopoietic stem cells. PNAS USA 108, E1408-1416, doi:10.1073/pnas.1115050108 (2011).

Fujii, S., Shimizu, K., Kronenberg, M. & Steinman, R. M. Prolonged IFN-gamma-producing NKT response induced with alpha-galactosylceramide-loaded DCs. Nat Immunol 3, 867-874, doi:10.1038/ni827 (2002).

Lockridge, J. L. et al. Analysis of the CD1 antigen presenting system in humanized SCID mice. PLoS One 6, e21701, doi:10.1371/journal.pone.0021701 (2011).

Sondergaard, J. N. et al. Differential sensitivity of melanoma cell lines with BRAFV600E mutation to the specific Raf inhibitor PLX4032. J Transl Med 8, 39, doi:10.1186/1479-5876-8-39 (2010).

Godfrey, D. I. & Berzins, S. P. Control points in NKT-cell development. Nat Rev Immunol 7, 505-518, doi:10.1038/nri2116 (2007).

Watarai, H., Nakagawa, R., Omori-Miyake, M., Dashtsoodol, N. & Taniguchi, M. Methods for detection, isolation and culture of mouse and human invariant NKT cells. Nat Protoc 3, 70-78, doi:10.1038/nprot.2007.515 (2008).

Mattarollo, S. R. et al. NKT cell adjuvant-based tumor vaccine for treatment of myc oncogene-driven mouse B-cell lymphoma. Blood 120, 3019-3029, doi:10.1182/blood-2012-04-426643 (2012).

Sznol, M. & Chen, L. Antagonist antibodies to PD-1 and B7-H1 (PD-L1) in the treatment of advanced human cancer. Clinical cancer research: an official journal of the American Association for Cancer Research 19, 1021-1034, doi:10.1158/1078-0432.CCR-12-2063 (2013).

Morrison, S. J., Uchida, N. & Weissman, I. L. The biology of hematopoietic stem cells. Annu Rev Cell Dev Biol 11, 35-71, doi:10.1146/annurev.cb.11.110195.000343 (1995).

Baltimore, D., Witte, O. N., Yang, L., Economou, J. & Ribas, A. Overcoming barriers to programming a therapeutic cellular immune response to fight melanoma. Pigment Cell Melanoma Res 23, 288-289, doi:10.1111/j.1755-148X.2010.00666.x (2010).

Chodon, T. et al. Adoptive transfer of MART-1 T-cell receptor transgenic lymphocytes and dendritic cell vaccination in patients with metastatic melanoma. Clinical cancer research: an official journal of the American Association for Cancer Research 20, 2457-2465, doi:10.1158/1078-0432.CCR-13-3017 (2014).

O'Connell, R. M. et al. Lentiviral vector delivery of human interleukin-7 (hIL-7) to human immune system (HIS) mice expands T lymphocyte populations. PLoS One 5, e12009, doi:10.1371/journal.pone.0012009 (2010).

Chung B. A. H, G. S., Blumberg G., Klein S., Zhu J., Parekh C., Arumugam B., Yang O., Crooks G. M. Engineering the human thymic microenvironment to manipulate thymopoiesis in vivo. Stem Cells 32(9):2386-2396 (2014).

Blumenthal, M. et al. Effective suicide gene therapy for leukemia in a model of insertional oncogenesis in mice. Molecular therapy: the journal of the American Society of Gene Therapy 15, 183-192, doi:10.1038/sj.mt.6300015 (2007).

Bendelac, A., Savage, P. B. & Teyton, L. The biology of NKT cells. Annu Rev Immunol 25, 297-336 (2007).

Luo, X. M. et al. Engineering human hematopoietic stem/progenitor cells to produce a broadly neutralizing anti-HIV antibody after in vitro maturation to human B lymphocytes. Blood 113, 1422-31 (2009).

Hur, E. M. et al. Inhibitory effect of HIV-specific neutralizing IgA on mucosal transmission of HIV in humanized mice. Blood 120, 4571-82 (2012).

Sun et al. Invariant natural killer T cells generated from human adult hematopoietic stem-progenitor cells are poly-functional. Cytokine 72:48-57 (2015).

Tian et al. The development of genetically modified K562 cells as artificial antigen presenting cells for NKT cells J. Immunol., 190: 45.3 (2013).

All scientific and technical terms used in this application have meanings commonly used in the art unless otherwise specified.

As used herein, the term "subject" includes humans and non-human animals. The term "non-human animal" includes all vertebrates, e.g., mammals and non-mammals, such as non-human primates, horses, sheep, dogs, cows, pigs, chickens, and other veterinary subjects and test animals.

The use of the singular can include the plural unless specifically stated otherwise. As used in the specification and the appended claims, the singular forms "a", "an", and "the" can include plural referents unless the context clearly dictates otherwise. The use of "or" can mean "and/or" unless stated otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

SEQUENCE LISTING

```
<160> NUMBER OF SEQ ID NOS: 62

<210> SEQ ID NO 1
<211> LENGTH: 3
<212> TYPE: DNA
<213> ORGANISM: Mus musculus

<400> SEQUENCE: 1 gtg                                                                        3
```

```
<210> SEQ ID NO 2
<211> LENGTH: 3
<212> TYPE: DNA
<213> ORGANISM: Mus musculus

<400> SEQUENCE: 2 gcc                                                                      3

<210> SEQ ID NO 3
<211> LENGTH: 3
<212> TYPE: DNA
<213> ORGANISM: Mus musculus

<400> SEQUENCE: 3 gcc                                                                      3

<210> SEQ ID NO 4
<211> LENGTH: 3
<212> TYPE: DNA
<213> ORGANISM: Mus musculus

<400> SEQUENCE: 4 gcc                                                                      3

<210> SEQ ID NO 5

<400> SEQUENCE: 5

000

<210> SEQ ID NO 6
<211> LENGTH: 3
<212> TYPE: DNA
<213> ORGANISM: Mus musculus

<400> SEQUENCE: 6 gcc                                                                      3

<210> SEQ ID NO 7
<211> LENGTH: 3
<212> TYPE: DNA
<213> ORGANISM: Homo sapiens

<400> SEQUENCE: 7 gtg                                                                      3

<210> SEQ ID NO 8
<211> LENGTH: 3
<212> TYPE: DNA
<213> ORGANISM: Homo sapiens

<400> SEQUENCE: 8 agc                                                                      3

<210> SEQ ID NO 9
<211> LENGTH: 3
<212> TYPE: DNA
<213> ORGANISM: Homo sapiens

<400> SEQUENCE: 9 agc                                                                      3

<210> SEQ ID NO 10
```

```
<211> LENGTH: 3
<212> TYPE: DNA
<213> ORGANISM: Homo sapiens

<400> SEQUENCE: 10 agc                                                                 3

<210> SEQ ID NO 11
<211> LENGTH: 3
<212> TYPE: DNA
<213> ORGANISM: Homo sapiens

<400> SEQUENCE: 11 agc                                                                 3

<210> SEQ ID NO 12
<211> LENGTH: 3
<212> TYPE: DNA
<213> ORGANISM: Homo sapiens

<400> SEQUENCE: 12 agc                                                                 3

<210> SEQ ID NO 13
<211> LENGTH: 3
<212> TYPE: DNA
<213> ORGANISM: Homo sapiens

<400> SEQUENCE: 13 agc                                                                 3

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gggagatact cagcaactct ggataaagat gc                                32

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccagattcca tggttttcgg cacattg                                      27

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggagatatcc ctgatggata caaggcctcc                                   30

<210> SEQ ID NO 17
```

<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gggtagcctt tgtttgttt gcaatctct                                     29

<210> SEQ ID NO 18
<211> LENGTH: 831
<212> TYPE: DNA
<213> ORGANISM: Homo sapiens

<400> SEQUENCE: 18
atgaaaaagc atctgacgac cttcttggtg attttgtggc tttattttta tagggggaat    60
ggcaaaaacc aagtggagca gagtcctcag tccctgatca tcctggaggg aaagaactgc   120
actcttcaat gcaattatac agtgagcccc ttcagcaact taaggtggta taagcaagat   180
actgggagag gtcctgtttc cctgacaatc atgactttca gtgagaacac aaagtcgaac   240
ggaagatata cagcaactct ggatgcagac acaaagcaaa gctctctgca catcacagcc   300
tcccagctca gcgattcagc tcctacatc tgtgtggtga gcgacagagg ctcaaccctg   360
gggaggctat actttggaag aggaactcag ttgactgtct ggcctgatat ccagaaccct   420
gaccctgccg tgtaccagct gagagactct aaatccagtg acaagtctgt ctgcctattc   480
accgattttg attctcaaac aaatgtgtca caaagtaagg attctgatgt gtatatcaca   540
gacaaaactg tgctagacat gaggtctatg gacttcaaga gcaacagtgc tgtggcctgg   600
agcaacaaat ctgactttgc atgtgcaaac gccttcaaca acagcattat tccagaagac   660
accttcttcc ccagcccaga aagttcctgt gatgtcaagc tggtcgagaa aagctttgaa   720
acagatacga acctaaactt tcaaaaacctg tcagtgattg ggttccgaat cctcctcctg   780
aaagtggccg ggtttaatct gctcatgacg ctgcggctgt ggtccagctg a             831

<210> SEQ ID NO 19
<211> LENGTH: 831
<212> TYPE: DNA
<213> ORGANISM: Homo sapiens

<400> SEQUENCE: 19
atgaaaaagc atctgacaac attcctggtc attctgtggc tgtacttcta ccgaggcaac    60
ggcaaaaatc aggtggagca gtccccacag tccctgatca ttctggaggg gaagaactgc   120
actctgcagt gtaattacac cgtgtctccc tttagtaacc tgcgctggta taaacaggac   180
accggacgag gaccccgtgag cctgacaatc atgactttct cagagaacac aaagagcaat   240
ggacggtaca ccgctacact ggacgcagat accaaacaga gctccctgca catcacagca   300
tctcagctgt cagatagcgc ctcctacatt tgcgtggtct ctgaccgagg gagtaccctg   360
ggccgactgt attttggaag ggggacccag ctgacagtgt ggcccgacat ccagaaccca   420
gatcccgccg tctaccagct gcgcgacagc aagtctagtg ataaaagcgt gtgcctgttc   480
acagactttg attctcagac taatgtgtct cagagtaagg acagtgacgt gtacattact   540
gacaaaaccg tcctggatat gaggagcatg gacttcaagt caaacagcgc cgtggcttgg   600
tcaaacaaga gcgacttcgc atgcgccaat gcttttaaca attcaatcat tccagaggat   660
accttctttc ctagcccaga atcaagctgt gacgtgaagc tggtcgagaa aagtttcgaa   720

-continued

```
actgatacca acctgaattt tcagaacctg tctgtgatcg gcttcagaat cctgctgctg      780
aaggtcgccg gctttaatct gctgatgaca ctgagactgt ggtcctcttg a              831
```

<210> SEQ ID NO 20
<211> LENGTH: 276
<212> TYPE: PRT
<213> ORGANISM: Homo sapiens

<400> SEQUENCE: 20

```
Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
            20                  25                  30

Ile Ile Leu Glu Gly Lys Asn Cys Thr Leu Gln Cys Asn Tyr Thr Val
        35                  40                  45

Ser Pro Phe Ser Asn Leu Arg Trp Tyr Lys Gln Asp Thr Gly Arg Gly
    50                  55                  60

Pro Val Ser Leu Thr Ile Met Thr Phe Ser Glu Asn Thr Lys Ser Asn
65                  70                  75                  80

Gly Arg Tyr Thr Ala Thr Leu Asp Ala Asp Thr Lys Gln Ser Ser Leu
                85                  90                  95

His Ile Thr Ala Ser Gln Leu Ser Asp Ser Ala Ser Tyr Ile Cys Val
            100                 105                 110

Val Ser Asp Arg Gly Ser Thr Leu Gly Arg Leu Tyr Phe Gly Arg Gly
        115                 120                 125

Thr Gln Leu Thr Val Trp Pro Asp Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275
```

<210> SEQ ID NO 21
<211> LENGTH: 960
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (337)..(426)
<223> OTHER INFORMATION: This region may encompass one of the following
      sequences:

```
    "GTAGCGGTTGGGCCCCAAGAGACCCAGTACTTCGGGCCAGGCACGCGGCTCCTGGTGCTC" or
    "GTGGCAGTCGGACCTCAGGAGACCCAGTACTTCGGACCCGGCACCCGCCTGCTGGTGCTG" or
    "AGTGGGCCAGGGTACGAGCAGTACTTCGGGCCGGGCACCAGGCTCACGGTCACA"
<220> FEATURE:
<221> NAME/KEY: modified_base
<222> LOCATION: (337)..(426)
<223> OTHER INFORMATION: CONT. FROM ABOVE: or
    "TCAGGACCCGGCTACGAGCAGTATTTCGGCCCCGGAACTCGGCTGACCGTGACC" or
    "AGTCCCCAATTAAACACTGAAGCTTTCTTTGGACAAGGCACCAGACTCACAGTTGTA" or
    "TCTCCACAGCTGAACACCGAGGCCTTCTTCGGGCAGGGCACAAGGCTTACCGTGGTG" or
    "AGTGAATTGCGGGCGCTCGGGCCCAGCTCCTATAATTCACCCCTCCACTTT"
<220> FEATURE:
<221> NAME/KEY: modified_base
<222> LOCATION: (337)..(426)
<223> OTHER INFORMATION: CONT. FROM ABOVE: GGGAACGGGACCAGGCTCACTGTGACA"
    or "TCCGAACTCCGAGCCCTGGGGCCTAGCTCCTACAATAGCCCCCTGCACTTTGGCAACGGAAC
    CAGGCTGACGGTCACC" or "AGTGAACAGGGGACTACTGCGGGAGCTTTCTTTGGACAAGGCAC
    CAGACTCACAGTTGTA" or "TCCGAACAGGGAACCACAGCAGGAGCCTTCTTCGGTCAGGGAAC
    AAGACTGACAGTCGTG"
<220> FEATURE:
<221> NAME/KEY: modified_base
<222> LOCATION: (337)..(426)
<223> OTHER INFORMATION: CONT. FROM ABOVE: or "AGTGAGTCACGACATGCGACAGGAA
    ACACCATATATTTTGGAGAGGGAAGTTGGCTCACTGTTGTA" or "AGCGAGAGCAGGCACGCAA
    CCGGGAACACCATATACTTTGGCGAGGGCTCCTGGCTGACTGTGGTG" or "AGTGTACCCGGGA
    ACGACAGGGGCAATGAAAAACTGTTTTTTGGCAGTGGAACCCAGCTCTCTGTCTTG" or "TCCG
    TGCCTGGCAAC
<220> FEATURE:
<221> NAME/KEY: modified_base
<222> LOCATION: (337)..(426)
<223> OTHER INFORMATION: CONT. FROM ABOVE: GATAGAGGTAACGAGAAGCTGTTTTTCGG
    ATCCGGCACACAGCTGTCTGTCCTG" or "AGTGAAGGGGGGGGCCTTAAGCTAGCCAAAAACAT
    TCAGTACTTCGGCGCCGGGACCCGGCTCTCAGTGCTG" or "AGTGAGGGAGGGGACTGAAGCT
    GGCTAAGAATATTCAGTACTTCGGCGCCGGCACTAGACTGTCTGTGCTG" or "AGTGAATTCGC
    CTCTTCGGTACGTG
<220> FEATURE:
<221> NAME/KEY: modified_base
<222> LOCATION: (337)..(426)
<223> OTHER INFORMATION: CONT. FROM ABOVE: GAAACACCATATATTTTGGAGAGGGAAGT
    TGGCTCACTGTTGTA" or "TCTGAGTTCGCGAGCAGCGTCCGGGGTAATACCATTTACTTCGGG
    GAAGGCAGCTGGCTGACCGTGGTG" or "AGTGCGGCATTAGGCCGGGAGACCCAGTACTTCGGG
    CCAGGCACGCGGCTCCTGGTGCTC" or "TCTGCAGCCCTTGGCCGAGAGACTCAGTACTTCGGC
    CCTGGCACAAG
<220> FEATURE:
<221> NAME/KEY: modified_base
<222> LOCATION: (337)..(426)
<223> OTHER INFORMATION: CONT. FROM ABOVE: ACTGCTCGTGCTC" or "AGTGCCTCCG
    GGGGTGAATCCTACGAGCAGTACTTCGGGCCGGGCACCAGGCTCACGGTCACA" or "AGCGCCT
    CCGGAGGAGAGTCATACGAACAGTATTTCGGCCCTGGCACACGCCTCACTGTGACC" or "AGCG
    GTCGGGTCTCGGGGGGCGATTCCCTCATAGCGTTTCTAGGCCAAGAGACCCAGTACTTCGGGCCAG
    GCACGCGGCTCCTGG
<220> FEATURE:
<221> NAME/KEY: modified_base
<222> LOCATION: (337)..(426)
<223> OTHER INFORMATION: CONT. FROM ABOVE: TGCTC" or "TCAGGACGAGTGTCCGGA
    GGGGATAGCCTCATCGCATTTCTGGGGCAGGAAACTCAGTACTTCGGACCCGGAACACGCCTCCTG
    GTGCTG" or "AGTGTACCCGGGAACGACAGGGGCAATGAAAAACTGTTTTTTGGCAGTGGAACC
    CAGCTCTCTGTCTTG" or "TCCGTGCCTGGCAACGATAGAGGTAACGAGAAGCTGTTTTTCGGA
    TCCGGCACACAGCTGT
<220> FEATURE:
<221> NAME/KEY: modified_base
<222> LOCATION: (337)..(426)
<223> OTHER INFORMATION: CONT. FROM ABOVE: CTGTCCTG"

<400> SEQUENCE: 21
atgactatca ggctcctctg ctacatgggc ttttatttc tgggggcagg cctcatggaa      60
gctgacatct accagacccc aagatacctt gttatagggg caggaaagaa gatcactctg    120
gaatgttctc aaaccatggg ccatgacaaa atgtactggt atcaacaaga tccaggaatg    180
gaactacacc tcatccacta ttcctatgga gttaattcca cagagaaggg agatctttcc    240
tctgagtcaa cagtctccag aataaggacg gagcattttc ccctgaccct ggagtctgcc    300
aggccctcac atacctctca gtacctctgt gccagcnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
```
nnnnnngagg acctgaacaa ggtgttccca cccgaggtcg ctgtgtttga gccatcagaa    480
gcagagatct cccacaccca aaaggccaca ctggtgtgcc tggccacagg cttcttccct    540
gaccacgtgg agctgagctg gtgggtgaat gggaaggagg tgcacagtgg ggtcagcacg    600
gacccgcagc ccctcaagga gcagcccgcc tcaatgact ccagatactg cctgagcagc    660
cgcctgaggg tctcggccac cttctggcag aacccccgca accacttccg ctgccaagtc    720
cagttctacg ggctctcgga gaatgacgag tggacccagg atagggccaa acccgtcacc    780
cagatcgtca gcgccgaggc ctggggtaga gcagactgtg gctttacctc ggtgtcctac    840
cagcaagggg tcctgtctgc caccatcctc tatgagatcc tgctagggaa ggccaccctg    900
tatgctgtgc tggtcagcgc ccttgtgttg atggccatgg tcaagagaaa ggatttctga    960

<210> SEQ ID NO 22
<211> LENGTH: 960
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (337)..(426)
<223> OTHER INFORMATION: This region may encompass one of the following
      sequences:
      "GTAGCGGTTGGGCCCCAAGAGACCCAGTACTTCGGGCCAGGCACGCGGCTCCTGGTGCTC" or
      "GTGGCAGTCGGACCTCAGGAGACCCAGTACTTCGGACCCGGCACCCGCCTGCTGGTGCTG" or
      "AGTGGGCCAGGGTACGAGCAGTACTTCGGGCCGGGCACCAGGCTCACGGTCACA"
<220> FEATURE:
<221> NAME/KEY: modified_base
<222> LOCATION: (337)..(426)
<223> OTHER INFORMATION: CONT. FROM ABOVE: or
      "TCAGGACCCGGCTACGAGCAGTATTTCGGCCCCGGAACTCGGCTGACCGTGACC" or
      "AGTCCCCAATTAAACACTGAAGCTTTCTTTGGACAAGGCACCAGACTCACAGTTGTA" or
      "TCTCCACAGCTGAACACCGAGGCCTTCTTCGGGCAGGGCACAAGGCTTACCGTGGTG" or
      "AGTGAATTGCGGGCGCTCGGGCCCAGCTCCTATAATTCACCCCTCCACTTT
<220> FEATURE:
<221> NAME/KEY: modified_base
<222> LOCATION: (337)..(426)
<223> OTHER INFORMATION: CONT. FROM ABOVE: GGGAACGGGACCAGGCTCACTGTGACA"
      or "TCCGAACTCCGAGCCCTGGGGCCTAGCTCCTACAATAGCCCCCTGCACTTTGGCAACGGAAC
      CAGGCTGACGGTCACC" or "AGTGAACAGGGGACTACTGCGGGAGCTTTCTTTGGACAAGGCAC
      CAGACTCACAGTTGTA" or "TCCGAACAGGGAACCACAGCAGGAGCCTTCTTCGGTCAGGGAAC
      AAGACTGACAGTCGTG"
<220> FEATURE:
<221> NAME/KEY: modified_base
<222> LOCATION: (337)..(426)
<223> OTHER INFORMATION: CONT. FROM ABOVE: or "AGTGAGTCACGACATGCGACAGGAA
      ACACCATATATTTTGGAGAGGGAAGTTGGCTCACTGTTGTA" or "AGCGAGAGCAGGCACGCAA
      CCGGGAACACCATATACTTTGGCGAGGGCTCCTGGCTGACTGTGGTG" or "AGTGTACCCGGGA
      ACGACAGGGGCAATGAAAAACTGTTTTTTGGCAGTGGAACCCAGCTCTCTGTCTTG" or
      "TCCGTGCCTGGCAAC
<220> FEATURE:
<221> NAME/KEY: modified_base
<222> LOCATION: (337)..(426)
<223> OTHER INFORMATION: CONT. FROM ABOVE: GATAGAGGTAACGAGAAGCTGTTTTTCGG
      ATCCGGCACACAGCTGTCTGTCCTG" or "AGTGAAGGGGGGGCCTTAAGCTAGCCAAAAACAT
      TCAGTACTTCGGCGCCGGGACCCGGCTCTCAGTGCTG" or "AGTGAGGGAGGGGGACTGAAGCT
      GGCTAAGAATATTCAGTACTTCGGCGCCGGCACTAGACTGTCTGTGCTG" or "AGTGAATTCGC
      CTCTTCGGTACGTG
<220> FEATURE:
<221> NAME/KEY: modified_base
<222> LOCATION: (337)..(426)
<223> OTHER INFORMATION: CONT. FROM ABOVE: GAAACACCATATATTTTGGAGAGGGAAGT
      TGGCTCACTGTTGTA" or "TCTGAGTTCGCGAGCAGCGTCCGGGGTAATACCATTTACTTCGGG
      GAAGGCAGCTGGCTGACCGTGGTG" or "AGTGCGGCATTAGGCCGGGAGACCCAGTACTTCGGG
      CCAGGCACGCGCGGCTCCTGGTGCTC" or "TCTGCAGCCCTTGGCCGAGAGACTCAGTACTTCGGC
      CCTGGCACAAG
<220> FEATURE:
<221> NAME/KEY: modified_base
<222> LOCATION: (337)..(426)
<223> OTHER INFORMATION: CONT. FROM ABOVE: ACTGCTCGTGCTC" or "AGTGCCTCCG

```
                GGGGTGAATCCTACGAGCAGTACTTCGGGCCGGGCACCAGGCTCACGGTCACA" or "AGCGCCT
                CCGGAGGAGAGTCATACGAACAGTATTTCGGCCCTGGCACACGCCTCACTGTGACC" or "AGCG
                GTCGGGTCTCGGGGGGCGATTCCCTCATAGCGTTTCTAGGCCAAGAGACCCAGTACTTCGGGCCAG
                GCACGCGGCTCCTGG
<220>  FEATURE:
<221>  NAME/KEY: modified_base
<222>  LOCATION: (337)..(426)
<223>  OTHER INFORMATION: CONT. FROM ABOVE: TGCTC" or "TCAGGACGAGTGTCCGGA
                GGGGATAGCCTCATCGCATTTCTGGGGCAGGAAACTCAGTACTTCGGACCCGGAACACGCCTCCTG
                GTGCTG" or "AGTGTACCCGGGAACGACAGGGGCAATGAAAAACTGTTTTTTGGCAGTGGAACC
                CAGCTCTCTGTCTTG" or "TCCGTGCCTGGCAACGATAGAGGTAACGAGAAGCTGTTTTTCGGA
                TCCGGCACACAGCTGT
<220>  FEATURE:
<221>  NAME/KEY: modified_base
<222>  LOCATION: (337)..(426)
<223>  OTHER INFORMATION: CONT. FROM ABOVE: CTGTCCTG"

<400>  SEQUENCE: 22 atgaccatcc ggctgctgtg ctacatgggc ttctattttc tggggcagg cctgatggaa        60 gccgacatct accagactcc cagataccct gtcatcggaa ccgggaagaa aattacactg      120
gagtgttccc agacaatggg ccacgataag atgtactggt atcagcagga ccctgggatg      180
gaactgcacc tgatccatta ctcctatggc gtgaactcta ccgagaaggg cgacctgagc      240
agcgaatcca ccgtctctcg aattaggaca gagcactttc ctctgactct ggaaagcgcc      300
cgaccaagtc atacatcaca gtacctgtgc gctagcnnnn nnnnnnnnnn nnnnnnnnn      360 nnnnnnnnnn nnnnnnnnnn nnnnnnnnnn nnnnnnnnnn nnnnnnnnnn nnnnnnnnnn      420
nnnnnngagg acctgaataa ggtgttcccc cctgaggtgg ctgtctttga accaagtgag      480
gcagaaattt cacatacaca gaaagccacc ctggtgtgcc tggctaccgg cttcttccc      540 gatcacgtgg agctgagctg gtgggtcaac ggcaaggaag tgcatagcgg agtctccaca      600
gacccacagc ccctgaaaga gcagcctgct ctgaatgatt ccagatactg cctgtctagt      660
agactgcggg tgtctgccac cttctggcag aacccaagga tcatttcag atgtcaggtg      720 cagttttatg gcctgagcga gaacgatgaa tggactcagg acagggctaa gccagtgacc      780
cagatcgtca gcgcagaggc ctggggaaga gcagactgcg ggtttacaag cgtgagctat      840
cagcagggcg tcctgagcgc cacaatcctg tacgaaattc tgctgggaaa ggccactctg      900
tatgctgtgc tggtctccgc tctggtgctg atggcaatgg tcaagcggaa agatttctga      960

<210>  SEQ ID NO 23
<211>  LENGTH: 319
<212>  TYPE: PRT
<213>  ORGANISM: Artificial Sequence
<220>  FEATURE:
<223>  OTHER INFORMATION: Description of Artificial Sequence: Synthetic
                polypeptide
<220>  FEATURE:
<221>  NAME/KEY: MOD_RES
<222>  LOCATION: (113)..(142)
<223>  OTHER INFORMATION: This region may encompass one of the following
                sequences: "SAALGRETQYFGPGTRLLVL" or "SASGGESYEQYFGPGTRLTVT" or
                "SEFASSVRGNTIYFGEGSWLTVV" or "SEGGGLKLAKNIQYFGAGTRLSVL" or
                "SELRALGPSSYNSPLHFGNGTRLTVT" or "SEQGTTAGAFFGQGTRLTVV" or
                "SESRHATGNTIYFGEGSWLTVV" or
<220>  FEATURE:
<221>  NAME/KEY: MOD_RES
<222>  LOCATION: (113)..(142)
<223>  OTHER INFORMATION: CONT. FROM ABOVE: "SGPGYEQYFGPGTRLTVT" or
                "SGRVSGGDSLIAFLGQETQYFGPGTRLLVL" or "SPQLNTEAFFGQGTRLTVV" or
                "SVPGNDRGNEKLFFGSGTQLSVL" or "SVPGNDRGNEKLFFGSGTQLSVL" or
                "VAVGPQETQYFGPGTRLLVL"

<400>  SEQUENCE: 23

Met Thr Ile Arg Leu Leu Cys Tyr Met Gly Phe Tyr Phe Leu Gly Ala
1               5                   10                  15
```

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Glu Asp
        130                 135                 140

Leu Asn Lys Val Phe Pro Pro Glu Val Ala Val Phe Glu Pro Ser Glu
145                 150                 155                 160

Ala Glu Ile Ser His Thr Gln Lys Ala Thr Leu Val Cys Leu Ala Thr
                165                 170                 175

Gly Phe Phe Pro Asp His Val Glu Leu Ser Trp Trp Val Asn Gly Lys
            180                 185                 190

Glu Val His Ser Gly Val Ser Thr Asp Pro Gln Pro Leu Lys Glu Gln
        195                 200                 205

Pro Ala Leu Asn Asp Ser Arg Tyr Cys Leu Ser Ser Arg Leu Arg Val
210                 215                 220

Ser Ala Thr Phe Trp Gln Asn Pro Arg Asn His Phe Arg Cys Gln Val
225                 230                 235                 240

Gln Phe Tyr Gly Leu Ser Glu Asn Asp Glu Trp Thr Gln Asp Arg Ala
                245                 250                 255

Lys Pro Val Thr Gln Ile Val Ser Ala Glu Ala Trp Gly Arg Ala Asp
            260                 265                 270

Cys Gly Phe Thr Ser Val Ser Tyr Gln Gln Gly Val Leu Ser Ala Thr
        275                 280                 285

Ile Leu Tyr Glu Ile Leu Leu Gly Lys Ala Thr Leu Tyr Ala Val Leu
290                 295                 300

Val Ser Ala Leu Val Leu Met Ala Met Val Lys Arg Lys Asp Phe
305                 310                 315

<210> SEQ ID NO 24
<211> LENGTH: 60
<212> TYPE: DNA
<213> ORGANISM: Homo sapiens

<400> SEQUENCE: 24
gtagcggttg ggccccaaga gacccagtac ttcgggccag gcacgcggct cctggtgctc    60

<210> SEQ ID NO 25
<211> LENGTH: 60
<212> TYPE: DNA
<213> ORGANISM: Homo sapiens

<400> SEQUENCE: 25
gtggcagtcg gacctcagga gacccagtac ttcggacccg gcacccgcct gctggtgctg    60

```
<210> SEQ ID NO 26
<211> LENGTH: 20
<212> TYPE: PRT
<213> ORGANISM: Homo sapiens

<400> SEQUENCE: 26

Val Ala Val Gly Pro Gln Glu Thr Gln Tyr Phe Gly Pro Gly Thr Arg
1               5                   10                  15

Leu Leu Val Leu
            20

<210> SEQ ID NO 27
<211> LENGTH: 54
<212> TYPE: DNA
<213> ORGANISM: Homo sapiens

<400> SEQUENCE: 27
agtgggccag ggtacgagca gtacttcggg ccgggcacca ggctcacggt caca         54

<210> SEQ ID NO 28
<211> LENGTH: 54
<212> TYPE: DNA
<213> ORGANISM: Homo sapiens

<400> SEQUENCE: 28
tcaggacccg gctacgagca gtatttcggc cccggaactc ggctgaccgt gacc         54

<210> SEQ ID NO 29
<211> LENGTH: 18
<212> TYPE: PRT
<213> ORGANISM: Homo sapiens

<400> SEQUENCE: 29

Ser Gly Pro Gly Tyr Glu Gln Tyr Phe Gly Pro Gly Thr Arg Leu Thr
1               5                   10                  15

Val Thr

<210> SEQ ID NO 30
<211> LENGTH: 57
<212> TYPE: DNA
<213> ORGANISM: Homo sapiens

<400> SEQUENCE: 30
agtccccaat aaacactga agctttcttt ggacaaggca ccagactcac agttgta      57

<210> SEQ ID NO 31
<211> LENGTH: 57
<212> TYPE: DNA
<213> ORGANISM: Homo sapiens

<400> SEQUENCE: 31
tctccacagc tgaacaccga ggccttcttc gggcagggca caaggcttac cgtggtg      57

<210> SEQ ID NO 32
<211> LENGTH: 19
<212> TYPE: PRT
<213> ORGANISM: Homo sapiens

<400> SEQUENCE: 32

Ser Pro Gln Leu Asn Thr Glu Ala Phe Phe Gly Gln Gly Thr Arg Leu
1               5                   10                  15

Thr Val Val
```

<210> SEQ ID NO 33
<211> LENGTH: 78
<212> TYPE: DNA
<213> ORGANISM: Homo sapiens

<400> SEQUENCE: 33
agtgaattgc gggcgctcgg gcccagctcc tataattcac ccctccactt tgggaacggg     60
accaggctca ctgtgaca                                                  78

<210> SEQ ID NO 34
<211> LENGTH: 78
<212> TYPE: DNA
<213> ORGANISM: Homo sapiens

<400> SEQUENCE: 34
tccgaactcc gagccctggg gcctagctcc tacaatagcc ccctgcactt tggcaacgga     60
accaggctga cggtcacc                                                  78

<210> SEQ ID NO 35
<211> LENGTH: 26
<212> TYPE: PRT
<213> ORGANISM: Homo sapiens

<400> SEQUENCE: 35

Ser Glu Leu Arg Ala Leu Gly Pro Ser Ser Tyr Asn Ser Pro Leu His
1               5                   10                  15

Phe Gly Asn Gly Thr Arg Leu Thr Val Thr
            20                  25

<210> SEQ ID NO 36
<211> LENGTH: 60
<212> TYPE: DNA
<213> ORGANISM: Homo sapiens

<400> SEQUENCE: 36
agtgaacagg ggactactgc gggagctttc tttggacaag gcaccagact cacagttgta     60

<210> SEQ ID NO 37
<211> LENGTH: 60
<212> TYPE: DNA
<213> ORGANISM: Homo sapiens

<400> SEQUENCE: 37
tccgaacagg gaaccacagc aggagccttc ttcggtcagg gaacaagact gacagtcgtg     60

<210> SEQ ID NO 38
<211> LENGTH: 20
<212> TYPE: PRT
<213> ORGANISM: Homo sapiens

<400> SEQUENCE: 38

Ser Glu Gln Gly Thr Thr Ala Gly Ala Phe Phe Gly Gln Gly Thr Arg
1               5                   10                  15

Leu Thr Val Val
            20

<210> SEQ ID NO 39
<211> LENGTH: 66
<212> TYPE: DNA
<213> ORGANISM: Homo sapiens

<400> SEQUENCE: 39

```
agtgagtcac gacatgcgac aggaaacacc atatattttg gagagggaag ttggctcact    60
gttgta                                                               66
```

<210> SEQ ID NO 40
<211> LENGTH: 66
<212> TYPE: DNA
<213> ORGANISM: Homo sapiens

<400> SEQUENCE: 40

```
agcgagagca ggcacgcaac cgggaacacc atatactttg gcgagggctc ctggctgact    60
gtggtg                                                               66
```

<210> SEQ ID NO 41
<211> LENGTH: 22
<212> TYPE: PRT
<213> ORGANISM: Homo sapiens

<400> SEQUENCE: 41

```
Ser Glu Ser Arg His Ala Thr Gly Asn Thr Ile Tyr Phe Gly Glu Gly
1               5                   10                  15

Ser Trp Leu Thr Val Val
            20
```

<210> SEQ ID NO 42
<211> LENGTH: 69
<212> TYPE: DNA
<213> ORGANISM: Homo sapiens

<400> SEQUENCE: 42

```
agtgtacccg ggaacgacag gggcaatgaa aaactgtttt ttggcagtgg aacccagctc    60
tctgtcttg                                                            69
```

<210> SEQ ID NO 43
<211> LENGTH: 69
<212> TYPE: DNA
<213> ORGANISM: Homo sapiens

<400> SEQUENCE: 43

```
tccgtgcctg gcaacgatag aggtaacgag aagctgtttt tcggatccgg cacacagctg    60
tctgtcctg                                                            69
```

<210> SEQ ID NO 44
<211> LENGTH: 23
<212> TYPE: PRT
<213> ORGANISM: Homo sapiens

<400> SEQUENCE: 44

```
Ser Val Pro Gly Asn Asp Arg Gly Asn Glu Lys Leu Phe Phe Gly Ser
1               5                   10                  15

Gly Thr Gln Leu Ser Val Leu
            20
```

<210> SEQ ID NO 45
<211> LENGTH: 72
<212> TYPE: DNA
<213> ORGANISM: Homo sapiens

<400> SEQUENCE: 45

```
agtgaagggg ggggccttaa gctagccaaa aacattcagt acttcggcgc cgggacccgg    60
```

```
ctctcagtgc tg                                                           72

<210> SEQ ID NO 46
<211> LENGTH: 72
<212> TYPE: DNA
<213> ORGANISM: Homo sapiens

<400> SEQUENCE: 46
agtgagggag ggggactgaa gctggctaag aatattcagt acttcggcgc cggcactaga      60
ctgtctgtgc tg                                                           72

<210> SEQ ID NO 47
<211> LENGTH: 24
<212> TYPE: PRT
<213> ORGANISM: Homo sapiens

<400> SEQUENCE: 47

Ser Glu Gly Gly Gly Leu Lys Leu Ala Lys Asn Ile Gln Tyr Phe Gly
1               5                   10                  15

Ala Gly Thr Arg Leu Ser Val Leu
            20

<210> SEQ ID NO 48
<211> LENGTH: 69
<212> TYPE: DNA
<213> ORGANISM: Homo sapiens

<400> SEQUENCE: 48
agtgaattcg cctcttcggt acgtggaaac accatatatt ttggagaggg aagttggctc      60
actgttgta                                                               69

<210> SEQ ID NO 49
<211> LENGTH: 69
<212> TYPE: DNA
<213> ORGANISM: Homo sapiens

<400> SEQUENCE: 49
tctgagttcg cgagcagcgt ccggggtaat accatttact tcggggaagg cagctggctg      60
accgtggtg                                                               69

<210> SEQ ID NO 50
<211> LENGTH: 23
<212> TYPE: PRT
<213> ORGANISM: Homo sapiens

<400> SEQUENCE: 50

Ser Glu Phe Ala Ser Ser Val Arg Gly Asn Thr Ile Tyr Phe Gly Glu
1               5                   10                  15

Gly Ser Trp Leu Thr Val Val
            20

<210> SEQ ID NO 51
<211> LENGTH: 60
<212> TYPE: DNA
<213> ORGANISM: Homo sapiens

<400> SEQUENCE: 51
agtgcggcat taggccggga gacccagtac ttcgggccag gcacgcggct cctggtgctc      60

<210> SEQ ID NO 52
<211> LENGTH: 60
```

```
<212> TYPE: DNA
<213> ORGANISM: Homo sapiens

<400> SEQUENCE: 52
tctgcagccc ttggccgaga gactcagtac ttcggccctg gcacaagact gctcgtgctc    60

<210> SEQ ID NO 53
<211> LENGTH: 20
<212> TYPE: PRT
<213> ORGANISM: Homo sapiens

<400> SEQUENCE: 53

Ser Ala Ala Leu Gly Arg Glu Thr Gln Tyr Phe Gly Pro Gly Thr Arg
1               5                   10                  15

Leu Leu Val Leu
            20

<210> SEQ ID NO 54
<211> LENGTH: 63
<212> TYPE: DNA
<213> ORGANISM: Homo sapiens

<400> SEQUENCE: 54
agtgcctccg ggggtgaatc ctacgagcag tacttcgggc cgggcaccag gctcacggtc    60
aca                                                                  63

<210> SEQ ID NO 55
<211> LENGTH: 63
<212> TYPE: DNA
<213> ORGANISM: Homo sapiens

<400> SEQUENCE: 55
agcgcctccg gaggagagtc atacgaacag tatttcggcc ctggcacacg cctcactgtg    60
acc                                                                  63

<210> SEQ ID NO 56
<211> LENGTH: 21
<212> TYPE: PRT
<213> ORGANISM: Homo sapiens

<400> SEQUENCE: 56

Ser Ala Ser Gly Gly Glu Ser Tyr Glu Gln Tyr Phe Gly Pro Gly Thr
1               5                   10                  15

Arg Leu Thr Val Thr
            20

<210> SEQ ID NO 57
<211> LENGTH: 90
<212> TYPE: DNA
<213> ORGANISM: Homo sapiens

<400> SEQUENCE: 57
agcggtcggg tctcgggggg cgattccctc atagcgtttc taggccaaga gacccagtac    60
ttcgggccag gcacgcggct cctggtgctc                                     90

<210> SEQ ID NO 58
<211> LENGTH: 90
<212> TYPE: DNA
<213> ORGANISM: Homo sapiens

<400> SEQUENCE: 58
```

```
tcaggacgag tgtccggagg ggatagcctc atcgcatttc tggggcagga aactcagtac      60
ttcggacccg gaacacgcct cctggtgctg                                      90

<210> SEQ ID NO 59
<211> LENGTH: 30
<212> TYPE: PRT
<213> ORGANISM: Homo sapiens

<400> SEQUENCE: 59

Ser Gly Arg Val Ser Gly Gly Asp Ser Leu Ile Ala Phe Leu Gly Gln
1               5                   10                  15

Glu Thr Gln Tyr Phe Gly Pro Gly Thr Arg Leu Leu Val Leu
            20                  25                  30

<210> SEQ ID NO 60
<211> LENGTH: 69
<212> TYPE: DNA
<213> ORGANISM: Homo sapiens

<400> SEQUENCE: 60
agtgtacccg ggaacgacag gggcaatgaa aaactgtttt ttggcagtgg aacccagctc     60
tctgtcttg                                                             69

<210> SEQ ID NO 61
<211> LENGTH: 69
<212> TYPE: DNA
<213> ORGANISM: Homo sapiens

<400> SEQUENCE: 61
tccgtgcctg gcaacgatag aggtaacgag aagctgtttt tcggatccgg cacacagctg     60
tctgtcctg                                                             69

<210> SEQ ID NO 62
<211> LENGTH: 23
<212> TYPE: PRT
<213> ORGANISM: Homo sapiens

<400> SEQUENCE: 62

Ser Val Pro Gly Asn Asp Arg Gly Asn Glu Lys Leu Phe Phe Gly Ser
1               5                   10                  15

Gly Thr Gln Leu Ser Val Leu
            20
```

What is claimed is:

1. A composition comprising an engineered cell having an exogenous invariant natural killer T cell receptor nucleic acid, wherein the engineered cell is derived from a progenitor cell into which has been incorporated the exogenous invariant natural killer T cell receptor nucleic acid and wherein the exogenous invariant natural killer T cell receptor nucleic acid is expressed as an invariant alpha chain polypeptide and a semi-invariant beta chain polypeptide.

2. The composition of claim 1, wherein the progenitor cell comprises a hematopoietic stem cell.

3. The composition of claim 1, wherein the exogenous invariant natural killer T cell receptor nucleic is incorporated into the progenitor cell by transduction.

4. The composition of claim 1, wherein the exogenous invariant natural killer T cell nucleic acid encodes a T cell receptor that recognizes alpha-galactosylceramide (α-Gal-Cer).

5. The composition of claim 1, wherein the engineered cell does not contain an exogenous oncogene.

6. The composition of claim 1, wherein the engineered cell is capable of producing one or more cytokines and/or chemokines.

7. The composition of claim 6, wherein the one or more cytokines and/or chemokines is selected from the group consisting of IFNγ, TNFα, TGFβ, GM-CSF, IL-2, IL-4, IL-5, IL-6, IL-10, IL-13, IL-17, IL-21, RANTES, Eotaxin, MIP-1α, and MIP-1β.

8. The composition of claim 1, wherein the engineered cell is derived from a progenitor cell that was expanded in vitro.

9. The composition of claim 1, wherein the progenitor cell is obtained from bone marrow, peripheral blood, amniotic fluid, or umbilical cord fluid.

10. The composition of claim 1, wherein the engineered cell is a human cell.

11. The composition of claim 1, wherein endogenous TCRs of the engineered cell are suppressed.

12. The composition of claim 1, wherein the progenitor cell is CD34+.

13. The composition of claim 1, wherein the engineered cell is a functional invariant Natural Killer T cell.

* * * * *